(12) United States Patent
Fahey et al.

(10) Patent No.: US 11,801,369 B2
(45) Date of Patent: Oct. 31, 2023

(54) ADJUSTABLE INTERATRIAL SHUNTS AND ASSOCIATED SYSTEMS AND METHODS

(71) Applicant: Shifamed Holdings, LLC, Campbell, CA (US)

(72) Inventors: Brian Fahey, Menlo Park, CA (US); Scott Robertson, Portland, OR (US); Peter Andriola, Castro Valley, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 18/006,567

(22) PCT Filed: Aug. 25, 2021

(86) PCT No.: PCT/US2021/047573
§ 371 (c)(1),
(2) Date: Jan. 23, 2023

(87) PCT Pub. No.: WO2022/046921
PCT Pub. Date: Feb. 2, 2022

(65) Prior Publication Data
US 2023/0191094 A1    Jun. 22, 2023

Related U.S. Application Data

(60) Provisional application No. 63/070,007, filed on Aug. 25, 2020.

(51) Int. Cl.
*A61M 27/00* (2006.01)
*A61B 17/00* (2006.01)
*A61B 17/11* (2006.01)

(52) U.S. Cl.
CPC . *A61M 27/002* (2013.01); *A61B 2017/00867* (2013.01); *A61B 2017/00929* (2013.01); *A61B 2017/1139* (2013.01)

(58) Field of Classification Search
CPC ....... A61M 27/002; A61B 2017/00867; A61B 2017/00929; A61B 2017/1139;
(Continued)

(56) References Cited

U.S. PATENT DOCUMENTS

| 3,874,388 A | 4/1975 | King et al. |
| 4,601,309 A | 7/1986 | Chang |

(Continued)

FOREIGN PATENT DOCUMENTS

| AU | 2005211243 | 8/2005 |
| AU | 2010344182 | 8/2012 |

(Continued)

OTHER PUBLICATIONS

International Search Report and Written Opinion received for International Application No. PCT/US22/34027, filed Jun. 17, 2022; Applicant: Shifamed Holdings, LLC; dated Oct. 25, 2022; 8 pages.

(Continued)

*Primary Examiner* — Brooke Labranche
(74) *Attorney, Agent, or Firm* — Perkins Coie LLP

(57) ABSTRACT

The present technology is generally directed to implantable medical devices and associated methods. For example, a system configured in accordance with embodiments of the present technology can include a body implantable into a patient and configured to undergo a shape change, the body having a conductive path with variable conductivity in portions thereof for selective and/or preferential heating. The body can be coupled with an energy source that can delivery energy to the body and/or conductive path, to promote the shape change in the body.

18 Claims, 11 Drawing Sheets

(58) Field of Classification Search
CPC .... A61L 31/14; A61L 31/022; A61L 2400/16; A61F 2/844; A61F 2/89; A61F 2/91; A61F 2210/0019; A61F 2250/0042; C22F 1/10
See application file for complete search history.

(56) References Cited

U.S. PATENT DOCUMENTS

| | | |
|---|---|---|
| 4,662,355 A | 5/1987 | Pieronne et al. |
| 4,705,507 A | 11/1987 | Boyles |
| 4,836,204 A | 6/1989 | Landymore et al. |
| 4,979,955 A | 12/1990 | Smith |
| 4,995,857 A | 2/1991 | Arnold |
| 5,186,431 A | 2/1993 | Tamari |
| 5,197,978 A | 3/1993 | Hess |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,556,386 A | 9/1996 | Todd |
| 5,584,803 A | 12/1996 | Stevens et al. |
| 5,597,377 A | 1/1997 | Aldea |
| 5,611,338 A | 3/1997 | Gallup |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,297 A | 4/1998 | Simon |
| 5,795,307 A | 8/1998 | Krueger |
| 5,810,836 A | 9/1998 | Hussein et al. |
| 5,824,071 A | 10/1998 | Nelson et al. |
| 5,916,193 A | 6/1999 | Stevens et al. |
| 5,941,850 A | 8/1999 | Shah et al. |
| 5,944,019 A | 8/1999 | Kundson et al. |
| 5,957,949 A | 9/1999 | Leonhardt et al. |
| 6,039,759 A | 3/2000 | Carpentier et al. |
| 6,077,298 A | 6/2000 | Tu et al. |
| 6,120,534 A | 9/2000 | Ruiz |
| 6,126,686 A | 10/2000 | Badylak et al. |
| 6,165,188 A | 12/2000 | Saadat et al. |
| 6,165,209 A | 12/2000 | Patterson et al. |
| 6,210,318 B1 | 4/2001 | Lederman |
| 6,217,541 B1 | 4/2001 | Yu |
| 6,240,322 B1 | 5/2001 | Peterfeso et al. |
| 6,242,762 B1 | 6/2001 | Brown et al. |
| 6,254,564 B1 | 7/2001 | Wilk et al. |
| 6,260,552 B1 | 7/2001 | Mortier et al. |
| 6,270,526 B1 | 8/2001 | Cox |
| 6,277,078 B1 | 8/2001 | Porat et al. |
| 6,302,892 B1 | 10/2001 | Wilk |
| 6,328,699 B1 | 12/2001 | Eigler et al. |
| 6,344,022 B1 | 2/2002 | Jarvik |
| 6,358,277 B1 | 3/2002 | Duran |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,478,776 B1 | 11/2002 | Rosenman et al. |
| 6,491,705 B2 | 12/2002 | Gifford, III et al. |
| 6,514,285 B1 | 2/2003 | Pinchasik |
| 6,527,698 B1 | 3/2003 | Kung et al. |
| 6,544,208 B2 | 4/2003 | Ethier et al. |
| 6,562,066 B1 | 5/2003 | Martin |
| 6,572,652 B2 | 6/2003 | Shaknovich |
| 6,589,198 B1 | 7/2003 | Soltanpour et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,783,499 B2 | 8/2004 | Schwartz |
| 6,909,920 B2 | 6/2005 | Lokhoff et al. |
| 6,911,043 B2 | 6/2005 | Myers et al. |
| 6,926,670 B2 | 8/2005 | Rich et al. |
| 7,001,409 B2 | 2/2006 | Amplatz |
| 7,011,095 B2 | 3/2006 | Wolf et al. |
| 7,056,294 B2 | 6/2006 | Khairkhahan et al. |
| 7,149,587 B2 | 12/2006 | Wardle et al. |
| 7,175,656 B2 | 2/2007 | Khairkhahan |
| 7,270,675 B2 | 9/2007 | Chun et al. |
| 7,294,115 B1 | 11/2007 | Wilk |
| 7,311,690 B2 | 12/2007 | Burnett |
| 7,311,730 B2 | 12/2007 | Gabbay |
| 7,317,951 B2 | 1/2008 | Schneider et al. |
| 7,389,134 B1 | 6/2008 | Karicherla et al. |
| 7,390,310 B2 | 6/2008 | McCusker et al. |
| 7,513,908 B2 | 4/2009 | Lattouf |
| 7,524,329 B2 | 4/2009 | Rucker |
| 7,524,330 B2 | 4/2009 | Berreklouw |
| 7,524,332 B2 | 4/2009 | Osborne et al. |
| 7,608,067 B2 | 10/2009 | Bonni |
| 7,615,010 B1 | 11/2009 | Najafi et al. |
| 7,617,001 B2 | 11/2009 | Penner et al. |
| 7,634,318 B2 | 12/2009 | Tran et al. |
| 7,658,747 B2 | 2/2010 | Forde et al. |
| 7,699,059 B2 | 4/2010 | Fonseca et al. |
| 7,736,327 B2 | 6/2010 | Wilk et al. |
| 7,780,725 B2 | 8/2010 | Haug et al. |
| 7,794,473 B2 | 9/2010 | Tessmer et al. |
| 7,806,921 B2 | 10/2010 | Hoffman |
| 7,860,579 B2 | 12/2010 | Goetzinger et al. |
| 7,892,246 B2 | 2/2011 | Akin et al. |
| 7,905,901 B2 | 3/2011 | Corcoran et al. |
| 7,922,764 B2 | 4/2011 | Gordy et al. |
| 7,938,840 B2 | 5/2011 | Golden et al. |
| 7,967,769 B2 | 6/2011 | Faul et al. |
| 7,988,724 B2 | 8/2011 | Salahieh et al. |
| 8,012,198 B2 | 9/2011 | Hill et al. |
| 8,016,877 B2 | 9/2011 | Seguin et al. |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,147,545 B2 | 4/2012 | Avior |
| 8,157,860 B2 | 4/2012 | McNamara et al. |
| 8,172,896 B2 | 5/2012 | McNamara et al. |
| 8,235,916 B2 | 8/2012 | Whiting et al. |
| 8,235,933 B2 | 8/2012 | Keren et al. |
| 8,246,677 B2 | 8/2012 | Ryan |
| 8,252,042 B2 | 8/2012 | McNamara et al. |
| 8,303,511 B2 | 11/2012 | Eigler et al. |
| 8,328,751 B2 | 12/2012 | Keren et al. |
| 8,348,996 B2 | 1/2013 | Tuval et al. |
| 8,398,708 B2 | 3/2013 | Meiri et al. |
| 8,460,366 B2 | 6/2013 | Rowe |
| 8,460,372 B2 | 6/2013 | McNamara et al. |
| 8,597,225 B2 | 12/2013 | Kapadia |
| 8,647,381 B2 | 2/2014 | Essinger et al. |
| 8,696,611 B2 | 4/2014 | Nitzan et al. |
| 8,740,962 B2 | 6/2014 | Finch et al. |
| 8,745,845 B2 | 6/2014 | Finch et al. |
| 8,747,458 B2 | 6/2014 | Tuval et al. |
| 8,752,258 B2 | 6/2014 | Finch et al. |
| 8,764,848 B2 | 7/2014 | Callaghan et al. |
| 8,882,697 B2 | 11/2014 | Celermajer et al. |
| 8,951,223 B2 | 2/2015 | McNamara et al. |
| 9,005,155 B2 | 4/2015 | Sugimoto |
| 9,034,034 B2 | 5/2015 | Nitzan et al. |
| 9,138,213 B2 | 9/2015 | Amin et al. |
| 9,204,842 B2 | 12/2015 | Mothilal et al. |
| 9,205,236 B2 | 12/2015 | McNamara et al. |
| 9,232,997 B2 | 1/2016 | Sugimoto et al. |
| 9,277,995 B2 | 3/2016 | Celermajer et al. |
| 9,358,371 B2 | 6/2016 | McNamara et al. |
| 9,456,812 B2 | 10/2016 | Finch et al. |

(56) References Cited

U.S. PATENT DOCUMENTS

| | | |
|---|---|---|
| 9,610,041 B2 | 4/2017 | Foster et al. |
| 9,629,715 B2 | 4/2017 | Nitzan et al. |
| 9,642,993 B2 | 5/2017 | McNamara et al. |
| 9,649,480 B2 | 5/2017 | Sugimoto et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,775,636 B2 | 10/2017 | Fazio et al. |
| 9,918,856 B2 | 3/2018 | Favier et al. |
| 9,937,036 B2 | 4/2018 | Sugimoto et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,076,403 B1 | 9/2018 | Eigler et al. |
| 10,188,375 B2 | 1/2019 | McNamara et al. |
| 10,207,087 B2 | 2/2019 | Keren |
| 10,251,740 B2 | 4/2019 | Eigler et al. |
| 10,292,690 B2 | 5/2019 | Celermajer et al. |
| 10,350,384 B2 | 7/2019 | Farnan et al. |
| 10,357,357 B2 | 7/2019 | Levi et al. |
| 10,368,981 B2 | 8/2019 | Nitzan et al. |
| 10,376,359 B2 | 8/2019 | Essinger et al. |
| 10,376,680 B2 | 8/2019 | McNamara et al. |
| 10,398,421 B2 | 9/2019 | Celermajer |
| 10,405,903 B1 | 9/2019 | Biesinger et al. |
| 10,413,284 B2 | 9/2019 | McNamara et al. |
| 10,413,286 B2 | 9/2019 | McNamara et al. |
| 10,463,477 B2 | 11/2019 | Forcucci et al. |
| 10,463,490 B2 | 11/2019 | Rottenberg et al. |
| 10,471,251 B1 | 11/2019 | Manicka |
| 10,478,594 B2 | 11/2019 | Yacoby et al. |
| 10,568,751 B2 | 2/2020 | McNamara |
| 10,588,611 B2 | 3/2020 | Magnin et al. |
| 10,610,210 B2 | 4/2020 | Finch et al. |
| 10,624,621 B2 | 4/2020 | Celermajer |
| 10,632,292 B2 | 4/2020 | Forcucci et al. |
| 10,639,459 B2 | 5/2020 | Nitzan et al. |
| 10,667,896 B2 | 6/2020 | Delaney, Jr. et al. |
| 10,675,450 B2 | 6/2020 | Finch |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,932,786 B2 | 3/2021 | McNamara et al. |
| 10,940,296 B2 | 3/2021 | Keren |
| 10,945,716 B2 | 3/2021 | Chen et al. |
| 11,135,410 B2 | 10/2021 | Finch et al. |
| 11,253,685 B2 | 2/2022 | Fahey et al. |
| 11,622,695 B1 | 4/2023 | Andriola et al. |
| 11,633,194 B2 | 4/2023 | Alexander et al. |
| 2002/0072656 A1 | 6/2002 | Vantassel et al. |
| 2002/0161427 A1 | 10/2002 | Rabkin et al. |
| 2002/0169371 A1 | 11/2002 | Gilderdale |
| 2002/0169475 A1 | 11/2002 | Gainor et al. |
| 2002/0177891 A1 | 11/2002 | Miles et al. |
| 2003/0125798 A1 | 7/2003 | Martin |
| 2003/0127090 A1 | 7/2003 | Gifford et al. |
| 2004/0016514 A1 | 1/2004 | Nien |
| 2004/0077988 A1 | 4/2004 | Tweden et al. |
| 2004/0088045 A1 | 5/2004 | Cox |
| 2004/0093075 A1 | 5/2004 | Kuehne |
| 2004/0143294 A1 | 7/2004 | Corcoran et al. |
| 2004/0147869 A1 | 7/2004 | Wolf et al. |
| 2004/0158143 A1 | 8/2004 | Flaherty et al. |
| 2004/0162514 A1 | 8/2004 | Alferness et al. |
| 2004/0186566 A1 | 9/2004 | Hindrichs et al. |
| 2004/0210190 A1 | 10/2004 | Kohler et al. |
| 2004/0215067 A1 | 10/2004 | Stiger et al. |
| 2004/0215323 A1 | 10/2004 | Stiger |
| 2005/0004641 A1 | 1/2005 | Pappu |
| 2005/0033351 A1 | 2/2005 | Newton |
| 2005/0060030 A1 | 3/2005 | Lashinski et al. |
| 2005/0101946 A1 | 5/2005 | Govari et al. |
| 2005/0148925 A1 | 7/2005 | Rottenberg et al. |
| 2005/0159789 A1 | 7/2005 | Brockway et al. |
| 2005/0165344 A1 | 7/2005 | Dobak, III |
| 2005/0192627 A1 | 9/2005 | Whisenant et al. |
| 2005/0204811 A1 | 9/2005 | Neff |
| 2005/0251212 A1 | 11/2005 | Kieval et al. |
| 2005/0288722 A1 | 12/2005 | Eigler et al. |
| 2006/0009810 A1 | 1/2006 | Mann et al. |
| 2006/0025857 A1 | 2/2006 | Bergheim et al. |
| 2006/0047205 A1 | 3/2006 | Ludomirsky et al. |
| 2006/0064135 A1 | 3/2006 | Brockway |
| 2006/0111660 A1 | 5/2006 | Wolf et al. |
| 2006/0116625 A1 | 6/2006 | Renati et al. |
| 2006/0200030 A1 | 9/2006 | White et al. |
| 2007/0010837 A1 | 1/2007 | Tanaka |
| 2007/0010852 A1 | 1/2007 | Blaeser et al. |
| 2007/0043435 A1 | 2/2007 | Seguin et al. |
| 2007/0088220 A1 | 4/2007 | Stahmann |
| 2007/0088223 A1 | 4/2007 | Mann et al. |
| 2007/0118039 A1 | 5/2007 | Bodecker et al. |
| 2007/0150019 A1 | 6/2007 | Youker et al. |
| 2007/0213813 A1 | 9/2007 | Von Segesser et al. |
| 2007/0282157 A1 | 12/2007 | Rottenberg et al. |
| 2008/0033527 A1 | 2/2008 | Nunez et al. |
| 2008/0097276 A1 | 4/2008 | Bertrand et al. |
| 2008/0108904 A1 | 5/2008 | Heil |
| 2008/0119891 A1 | 5/2008 | Miles et al. |
| 2008/0127689 A1 | 6/2008 | McCusker et al. |
| 2008/0171941 A1 | 7/2008 | Huelskamp et al. |
| 2008/0208083 A1 | 8/2008 | Lin et al. |
| 2008/0208286 A1 | 8/2008 | Kieval et al. |
| 2009/0025459 A1 | 1/2009 | Zhang et al. |
| 2009/0036975 A1 | 2/2009 | Ward et al. |
| 2009/0243956 A1 | 10/2009 | Keilman et al. |
| 2009/0270742 A1 | 10/2009 | Wolinsky et al. |
| 2009/0276040 A1 | 11/2009 | Rowe et al. |
| 2009/0281597 A1 | 11/2009 | Parramon et al. |
| 2010/0063375 A1 | 3/2010 | Kassab et al. |
| 2010/0076366 A1 | 3/2010 | Henderson, Sr. et al. |
| 2010/0076517 A1 | 3/2010 | Imran |
| 2010/0106028 A1 | 4/2010 | Penner et al. |
| 2010/0168672 A1 | 7/2010 | Carr |
| 2010/0179449 A1 | 7/2010 | Chow et al. |
| 2010/0241241 A1 | 9/2010 | McKnight et al. |
| 2010/0249560 A1 | 9/2010 | Levinson et al. |
| 2010/0262021 A1 | 10/2010 | Yadav et al. |
| 2010/0262036 A1 | 10/2010 | Najafi et al. |
| 2010/0275592 A1 | 11/2010 | Topliss et al. |
| 2010/0298930 A1 | 11/2010 | Orlov |
| 2011/0054515 A1 | 3/2011 | Bridgeman et al. |
| 2011/0082377 A1 | 4/2011 | Mahajan et al. |
| 2011/0218480 A1 | 9/2011 | Rottenberg et al. |
| 2011/0218481 A1 | 9/2011 | Rottenberg et al. |
| 2011/0257723 A1 | 10/2011 | McNamara |
| 2011/0264194 A1 | 10/2011 | Griswold |
| 2011/0282217 A1 | 11/2011 | Nashet |
| 2011/0295183 A1 | 12/2011 | Finch et al. |
| 2012/0053686 A1 | 3/2012 | McNamara et al. |
| 2012/0059431 A1 | 3/2012 | Williams et al. |
| 2012/0229272 A1 | 9/2012 | Jacob et al. |
| 2012/0265296 A1 | 10/2012 | McNamara et al. |
| 2012/0283773 A1 | 11/2012 | Van Tassel et al. |
| 2012/0290062 A1 | 11/2012 | McNamara et al. |
| 2013/0085350 A1 | 4/2013 | Schugt et al. |
| 2013/0123569 A1 | 5/2013 | Gross |
| 2013/0144379 A1 | 6/2013 | Najafi et al. |
| 2013/0178783 A1 | 7/2013 | Mcnamara et al. |
| 2013/0178784 A1 | 7/2013 | McNamara et al. |
| 2013/0190799 A1 | 7/2013 | Clark |
| 2013/0192611 A1 | 8/2013 | Taepke, II et al. |
| 2013/0197423 A1 | 8/2013 | Keren et al. |
| 2013/0211221 A1 | 8/2013 | Sunnarborg et al. |
| 2013/0253343 A1 | 9/2013 | Waldhauser et al. |
| 2013/0261531 A1 | 10/2013 | Gallagher et al. |
| 2014/0012342 A1 | 1/2014 | Penner et al. |
| 2014/0046427 A1 | 2/2014 | Michalak |
| 2014/0128795 A1 | 5/2014 | Keren et al. |
| 2014/0128796 A1 | 5/2014 | Keren et al. |

(56) References Cited

U.S. PATENT DOCUMENTS

| | | |
|---|---|---|
| 2014/0135647 A1 | 5/2014 | Wolf, II |
| 2014/0163449 A1 | 6/2014 | Rottenberg et al. |
| 2014/0213915 A1 | 7/2014 | Doan et al. |
| 2014/0213916 A1 | 7/2014 | Doan et al. |
| 2014/0213959 A1 | 7/2014 | Nitzan et al. |
| 2014/0222040 A1 | 8/2014 | Park et al. |
| 2014/0249616 A1 | 9/2014 | Strauss et al. |
| 2014/0277054 A1 | 9/2014 | McNamara et al. |
| 2014/0306807 A1 | 10/2014 | Rowland et al. |
| 2015/0034217 A1 | 2/2015 | Vad |
| 2015/0119796 A1 | 4/2015 | Finch |
| 2015/0148731 A1 | 5/2015 | McNamara et al. |
| 2015/0157268 A1 | 6/2015 | Winshtein et al. |
| 2015/0208929 A1 | 7/2015 | Rowland et al. |
| 2015/0223707 A1 | 8/2015 | Ludoph et al. |
| 2015/0230843 A1 | 8/2015 | Palmer et al. |
| 2015/0231387 A1 | 8/2015 | Harding et al. |
| 2016/0022423 A1* | 1/2016 | McNamara ......... A61M 27/002 604/9 |
| 2016/0089079 A1 | 3/2016 | Stein |
| 2016/0151179 A1 | 6/2016 | Favier et al. |
| 2016/0158561 A1 | 6/2016 | Reddy |
| 2016/0235999 A1 | 8/2016 | Nuta et al. |
| 2017/0014067 A1 | 1/2017 | Peppou et al. |
| 2017/0105635 A1 | 4/2017 | Cho et al. |
| 2017/0113026 A1 | 4/2017 | Finch |
| 2017/0312078 A1 | 11/2017 | Krivoruchko |
| 2017/0340460 A1 | 11/2017 | Rosen et al. |
| 2018/0014828 A1 | 1/2018 | Fonte et al. |
| 2018/0117341 A1 | 5/2018 | Kane et al. |
| 2018/0168463 A1 | 6/2018 | Morris et al. |
| 2018/0250014 A1 | 9/2018 | Melanson et al. |
| 2018/0256865 A1 | 9/2018 | Finch et al. |
| 2018/0262037 A1 | 9/2018 | Meskeus |
| 2018/0310839 A1 | 11/2018 | McCaffrey et al. |
| 2019/0000327 A1 | 1/2019 | Doan |
| 2019/0014993 A1 | 1/2019 | Kaiser |
| 2019/0015103 A1 | 1/2019 | Sharma |
| 2019/0021861 A1 | 1/2019 | Finch |
| 2019/0150758 A1 | 5/2019 | Bailey et al. |
| 2019/0167197 A1 | 6/2019 | Abuuassar et al. |
| 2019/0173505 A1 | 6/2019 | Koyama |
| 2019/0175883 A1 | 6/2019 | Wessler et al. |
| 2019/0192864 A1 | 6/2019 | Koop et al. |
| 2019/0254814 A1 | 8/2019 | Nitzan et al. |
| 2019/0262118 A1 | 8/2019 | Eigler et al. |
| 2019/0269392 A1 | 9/2019 | Celermajer et al. |
| 2019/0298556 A1 | 10/2019 | Bohn et al. |
| 2019/0307459 A1 | 10/2019 | Celermajer et al. |
| 2019/0328513 A1 | 10/2019 | Levi et al. |
| 2019/0336135 A1 | 11/2019 | Inouye et al. |
| 2019/0336163 A1 | 11/2019 | McNamara et al. |
| 2020/0008870 A1 | 1/2020 | Gruba et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |
| 2020/0188143 A1 | 6/2020 | McNamara |
| 2020/0196867 A1 | 6/2020 | Andersen et al. |
| 2020/0196876 A1 | 6/2020 | Minor et al. |
| 2020/0197178 A1 | 6/2020 | Vecchio |
| 2020/0229977 A1 | 7/2020 | Mixter et al. |
| 2020/0229981 A1 | 7/2020 | Mixter et al. |
| 2020/0229982 A1 | 7/2020 | Mixter et al. |
| 2020/0245991 A1 | 8/2020 | Celermajer |
| 2020/0253615 A1 | 8/2020 | Melanson et al. |
| 2020/0260991 A1 | 8/2020 | Rowlaud et al. |
| 2020/0261705 A1 | 8/2020 | Nitzan et al. |
| 2020/0268515 A1 | 8/2020 | Vettukattil et al. |
| 2020/0281611 A1 | 9/2020 | Kelly et al. |
| 2020/0315599 A1 | 10/2020 | Nae et al. |
| 2020/0368505 A1 | 11/2020 | Nae et al. |
| 2021/0030273 A1 | 2/2021 | Huang et al. |
| 2021/0038230 A1 | 2/2021 | Larsen et al. |
| 2021/0052378 A1 | 2/2021 | Nitzan et al. |
| 2021/0059527 A1 | 3/2021 | Najafi |
| 2021/0085935 A1 | 3/2021 | Fahey et al. |
| 2021/0100513 A1 | 4/2021 | Sahmauyar et al. |
| 2021/0100665 A1 | 4/2021 | Nae et al. |
| 2021/0121179 A1 | 4/2021 | Ben-David et al. |
| 2021/0145331 A1 | 5/2021 | Simpson et al. |
| 2021/0153776 A1 | 5/2021 | Minar et al. |
| 2021/0177508 A1 | 6/2021 | Kellerman |
| 2021/0205590 A1 | 7/2021 | Fahey et al. |
| 2021/0212638 A1 | 7/2021 | Golda et al. |
| 2021/0259732 A1 | 8/2021 | Dicicco et al. |
| 2021/0259829 A1 | 8/2021 | Quinn |
| 2021/0259839 A1 | 8/2021 | Cole et al. |
| 2021/0290214 A1 | 9/2021 | Cole et al. |
| 2021/0290356 A1 | 9/2021 | Srinkmann et al. |
| 2021/0298763 A1 | 9/2021 | Stahmann et al. |
| 2021/0299425 A1 | 9/2021 | Kume et al. |
| 2021/0299430 A1 | 9/2021 | Ratz et al. |
| 2021/0361238 A1 | 11/2021 | Bak-Boychuk et al. |
| 2021/0361257 A1 | 11/2021 | Eimer et al. |
| 2021/0370032 A1 | 12/2021 | Fahey et al. |
| 2021/0401418 A1 | 12/2021 | Dang et al. |
| 2022/0008014 A1 | 1/2022 | Rowe et al. |
| 2022/0039670 A1 | 2/2022 | Berrada et al. |
| 2022/0039671 A1 | 2/2022 | Fahey |
| 2022/0117555 A1 | 4/2022 | Zarbatauy et al. |
| 2022/0118228 A1 | 4/2022 | Fahey et al. |
| 2022/0143368 A1 | 5/2022 | Pulugurtha et al. |
| 2022/0151618 A1 | 5/2022 | Eigler et al. |
| 2022/0167861 A1 | 6/2022 | Stahmann |
| 2022/0184355 A1 | 6/2022 | Fahey et al. |
| 2022/0192677 A1 | 6/2022 | Wedul et al. |
| 2022/0218355 A1 | 7/2022 | Wedul et al. |
| 2022/0218964 A1 | 7/2022 | Fahey et al. |
| 2022/0226000 A1 | 7/2022 | Alexander et al. |
| 2022/0226623 A1 | 7/2022 | Fahey et al. |
| 2022/0240856 A1 | 8/2022 | Stahmann et al. |
| 2022/0265280 A1 | 8/2022 | Chamorro et al. |
| 2022/0313426 A1* | 10/2022 | Gifford, III ........... A61F 2/2418 |
| 2023/0084193 A1 | 3/2023 | Fahey et al. |
| 2023/0118243 A1 | 4/2023 | Fox et al. |
| 2023/0129883 A1 | 4/2023 | Andriola et al. |
| 2023/0158280 A1 | 5/2023 | Andriola et al. |
| 2023/0165672 A1 | 6/2023 | Fahey et al. |
| 2023/0200667 A1 | 6/2023 | Andriola et al. |
| 2023/0201545 A1 | 6/2023 | Alexander et al. |
| 2023/0201546 A1 | 6/2023 | Fahey et al. |

FOREIGN PATENT DOCUMENTS

| | | |
|---|---|---|
| AU | 2011332324 | 6/2013 |
| AU | 2012214279 | 8/2013 |
| AU | 2018228451 | 9/2019 |
| CA | 2785041 | 8/2011 |
| CA | 2786575 | 8/2011 |
| CA | 2818417 | 5/2012 |
| CA | 2955389 | 1/2016 |
| CA | 3054891 | 9/2018 |
| CN | 101415452 | 4/2009 |
| CN | 102458316 | 5/2012 |
| CN | 102905626 | 1/2013 |
| CN | 103458832 | 12/2013 |
| CN | 105662653 | 6/2016 |
| CN | 109646063 A | 4/2019 |
| CN | 110536657 | 12/2019 |
| EP | 1112044 | 1/2007 |
| EP | 2097012 | 9/2009 |
| EP | 2528646 | 12/2012 |
| EP | 2642954 | 10/2013 |
| EP | 2967867 | 1/2016 |
| EP | 3087953 | 11/2016 |
| EP | 3291773 | 3/2018 |
| EP | 3329860 | 6/2018 |
| EP | 3579907 | 12/2019 |
| EP | 3589238 | 1/2020 |
| EP | 3624701 | 3/2020 |
| EP | 2999412 | 5/2020 |
| EP | 3705154 | 9/2020 |
| EP | 3716877 | 10/2020 |

(56) References Cited

FOREIGN PATENT DOCUMENTS

| | | |
|---|---|---|
| EP | 3740163 | 11/2020 |
| EP | 3766431 | 1/2021 |
| EP | 3834737 | 6/2021 |
| EP | 3843618 | 7/2021 |
| EP | 3871626 | 9/2021 |
| EP | 3886761 | 10/2021 |
| EP | 3893731 | 10/2021 |
| EP | 3897369 | 10/2021 |
| IL | 176973 | 12/2006 |
| IL | 221127 | 9/2012 |
| IL | 226374 | 7/2013 |
| IL | 215975 | 11/2016 |
| IL | 227756 | 6/2017 |
| IL | 220201 | 8/2017 |
| IL | 253648 | 9/2017 |
| IL | 255379 | 12/2017 |
| IL | 252395 | 4/2020 |
| IN | 2011KN04472 | 7/2012 |
| IN | 2012KN01275 | 2/2013 |
| IN | 2013KN01954 | 11/2013 |
| IN | 2013CN06525 | 8/2014 |
| IN | 2012KN01988 | 8/2016 |
| JP | 2007527742 | 10/2007 |
| JP | 2010508093 | 3/2010 |
| JP | 2012196504 | 10/2012 |
| JP | 2013046784 | 3/2013 |
| JP | 2014503246 | 2/2014 |
| JP | 2014512869 | 5/2014 |
| JP | 2020509812 | 4/2020 |
| KR | 20010046155 | 6/2001 |
| WO | WO2005074367 | 8/2005 |
| WO | WO2007083288 | 7/2007 |
| WO | WO2008055301 | 5/2008 |
| WO | WO2010128501 | 11/2010 |
| WO | WO2010129089 | 11/2010 |
| WO | WO2011093941 | 8/2011 |
| WO | WO2011094521 | 8/2011 |
| WO | WO2012071075 | 5/2012 |
| WO | WO2012085913 | 6/2012 |
| WO | WO2012109557 | 8/2012 |
| WO | WO2013014539 | 1/2013 |
| WO | WO2013096965 | 6/2013 |
| WO | WO2014150106 | 9/2014 |
| WO | WO2014188279 | 11/2014 |
| WO | WO2016014821 | 1/2016 |
| WO | WO2016038115 | 3/2016 |
| WO | WO2016178171 | 11/2016 |
| WO | WO2018024868 | 2/2018 |
| WO | WO2018132549 | 7/2018 |
| WO | WO2018158747 | 9/2018 |
| WO | WO2019186101 | 2/2019 |
| WO | WO2019142152 | 7/2019 |
| WO | WO2019175401 | 9/2019 |
| WO | WO2019179447 | 9/2019 |
| WO | WO2019188917 | 10/2019 |
| WO | WO2019189079 | 10/2019 |
| WO | WO2019209420 | 10/2019 |
| WO | WO2020023514 | 1/2020 |
| WO | WO2020094085 | 5/2020 |
| WO | WO2020094087 | 5/2020 |
| WO | WO2020094094 | 5/2020 |
| WO | WO2020110048 | 6/2020 |
| WO | WO2020123338 | 6/2020 |
| WO | WO2020132678 | 6/2020 |
| WO | WO2020142515 | 7/2020 |
| WO | WO2020142613 | 7/2020 |
| WO | WO2020198694 | 10/2020 |
| WO | WO2020202046 | 10/2020 |
| WO | WO2020206366 | 10/2020 |
| WO | WO2020215090 | 10/2020 |
| WO | WO2020217194 | 10/2020 |
| WO | WO2020219265 | 10/2020 |
| WO | WO2020225698 | 11/2020 |
| WO | WO2020225757 | 11/2020 |
| WO | WO2020229636 | 11/2020 |
| WO | WO2020234751 | 11/2020 |
| WO | WO2020251700 | 12/2020 |
| WO | WO2020259492 | 12/2020 |
| WO | WO2021025905 | 2/2021 |
| WO | WO2021026485 | 2/2021 |
| WO | WO2021046753 | 3/2021 |
| WO | WO2021050589 | 3/2021 |
| WO | WO2021055264 | 3/2021 |
| WO | WO2021065873 | 4/2021 |
| WO | WO2021065874 | 4/2021 |
| WO | WO2021065875 | 4/2021 |
| WO | WO2021065912 | 4/2021 |
| WO | WO2021072315 | 4/2021 |
| WO | WO2021086707 | 5/2021 |
| WO | WO2021091566 | 5/2021 |
| WO | WO2021096766 | 5/2021 |
| WO | WO2021101707 | 5/2021 |
| WO | WO2021113670 | 6/2021 |
| WO | WO2021126699 | 6/2021 |
| WO | WO2021136252 | 7/2021 |
| WO | WO2021136261 | 7/2021 |
| WO | WO2021138041 | 7/2021 |
| WO | WO2021146342 | 7/2021 |
| WO | WO2021150765 | 7/2021 |
| WO | WO2021158559 | 8/2021 |
| WO | WO2021159001 | 8/2021 |
| WO | WO2021162888 | 8/2021 |
| WO | WO2021178636 | 9/2021 |
| WO | WO2021190547 | 9/2021 |
| WO | WO2021212011 | 10/2021 |
| WO | WO2021216964 | 10/2021 |
| WO | WO2021217055 | 10/2021 |
| WO | WO2021217059 | 10/2021 |
| WO | WO2021224736 | 11/2021 |
| WO | WO2022046921 | 3/2022 |
| WO | WO2022076601 | 4/2022 |
| WO | WO2022081980 | 4/2022 |
| WO | WO2022103973 | 5/2022 |
| WO | WO2022192280 | 9/2022 |
| WO | WO2022266465 | 12/2022 |
| WO | WO2022266503 | 12/2022 |
| WO | WO2022272131 | 12/2022 |
| WO | WO2023278725 | 1/2023 |

OTHER PUBLICATIONS

International Search Report and Written Opinion received for International Application No. PCT/US22/34995, filed Jun. 24, 2022; Applicant: Shifamed Holdings, LLC; dated Nov. 18, 2022; 17 pages.
Perk et al., "Catheter-based left atrial appendage occlusion procedure: role of echocardiography," published on behalf of the European Society of Cardiology, Sep. 8, 2011, 7 pages.
Collado et al, "Left Atrial Appendage Occlusion for Stroke Prevention in Nonvalvular Atrial Fibrillation," Journal of the American Heart Association, Jun. 2021, 18 pages.
International Search Report and Written Opinion received for International Application No. PCT/US21/47573, filed Aug. 25, 2021; Applicant: Shifamed Holdings, LLC; dated Feb. 3, 2022; 15 pages.
Kocaturk, O. et al., "Whole shaft visibility and mechanical performance for active MR catheters using copper-nitinol braided polymer tubes," Journal of Cardiovascular Magnetic Resonance. Aug. 12, 2009, vol. 11, No. 29, pp. 9, col. 1, In 5-6.
Hossain, M. et al. "In situ preparation of graphene-ZnO composites for enhanced graphite exfoliation and graphene-nylon-6 composite films," Journal of Applied Polymer Science, Dec. 5, 2016, vol. 134, No. 27, p. 8, In 15-16.
Ando et al., "Left ventricular decompression through a patent foramen ovale in a patient with hypertrophic cardiomyopathy: a case report," Cardiovascular Ultrasound volume Article No. 2 (2004).
Braunwald, Heart Disease, Chapter 6, 2015, p. 186.
Bridges et al., "The Society of Thoracic Surgeons practice guideline series: transmyocardial laser revascularization," The Annals of Thoracic Surgery, vol. 77, Issue 4, Apr. 2004, pp. 1494-1502.

(56) References Cited

OTHER PUBLICATIONS

Bristow et al., "Improvement in cardiac myocyte function by biological effects of medical therapy: A new concept in the treatment of heart failure," European Heart Journal, vol. 16, Issue suppl. F, Jul. 1995, pp. 20-31.
Case et al., "Relief of High Left-Atrial Pressure in Left-Ventricular Failure," Lancet, Oct. 17, 1964, pp. 841-842.
Coats et al., "Controlled trial of physical training in chronic heart failure. Exercise performance, hemodynamics, ventilation, and autonomic function," Circulation, 1992;85:2119-2131.
Davies et al., "Reduced contraction and altered frequency response of isolated ventricular myocytes from patients with heart failure," Circulation, (1995), 92:2540-2549, Circulation, (1995), 92:2540-2549.
Ennezat et al., "An unusual case of low-flow, low gradient severe aortic stenosis: Left-to-right shunt due to atrial septal defect," Cardiology, (2009), 113(2):146-148.
Ewert et al., "Masked Left Ventricular Restriction in Elderly Patients With Atrial Septal Defects: A Contraindication for Closure," Catheterization and Cardiovascular Interventions, 52: 177-180, 2001.
Ewert et al., "Acute left heart failure after interventional occlusion of an atrial septal defect," Z. Kardiol., Catheterization and Cardiovascular Interventions, Z. Kardiol., (May 2001), 90(5):362-366.
Geiran et al., "Changes in cardiac dynamics by opening an interventricular shunt in dogs," J. Surg. Res., (Jan. 1990), 48(1):6-12.
Gelernter-Yaniv et al., "Transcatheter closure of left-to-right interatrial shunts to resolve hypoxemia," Congenit. Heart Dis., (Jan. 2008), 31(1):47-53.
Gewillig et al., "Creation with a stent of an unrestrictive lasting atrial communication," Cardio. Young, (2002), 12(4):404-407.
Khositseth et al., "Transcatheter Amplatzer Device Closure of Atrial Septal Defect and Patent Foramen Ovale in Patients With Presumed Paradoxical Embolism," Mayo Clinic Proc., 79:35-41 (2004).
Kramer et al., "Controlled study of captopril in chronic heart failure: A rest and exercise hemodynamic study," Circulation, (1983), 67(4):807-816.
Lai et al., "Bidirectional shunt through a residual atrial septal defect after percutaneous transvenous mitral commissurotomy," Cardiology, (1993), 83(3):205-207.
Lemmer et al., "Surgical implications of atrial septal defect complicating aortic balloon valvuloplasty," Ann. thorac. Surg., (Aug. 1989), 48(2):295-297.
Park et al., "Blade atrial septostomy: collaborative study," Circulation, 66(2):258-266 (1982).
Roven et al., "Effect of Compromising Right Ventricular Function in Left Ventricular Failure by Means of Interatrial and Other Shunts," American Journal Cardiology, 24:209-219 (1969).
Salehian et al., "Improvements in Cardiac Form and Function After Transcatheter Closure of Secundum Atrial Septal Defects," Journal of the American College of Cardiology, 45(4):499-504 (2005).
Schmitto et al., "Chronic heart failure induced by multiple sequential coronary microembolization in sheep," The International Journal of Artificial Organs, 31(4):348-353 (2008).
Schubert et al., "Left ventricular conditioning in the elderly patient to prevent congestive heart failure after transcatheter closure of the atrial septal defect," Catheter Cardiovasc. Interv., (2005), 64(3):333-337.
Stormer et al., "Comparative study of in vitro flow characteristics between a human aortic valve and a designed aortic and six corresponding types of prosthetic heart valves," European Surgical Research, (1976), 8(2):117-131.
Stumper et al., "Modified technique of stent fenestration of the atrial septum, Heart," (2003), 89:1227-1230.
Trainor et al., "Comparative Pathology of an Implantable Left Atrial Pressure Sensor," ASAIO Journal, Clinical Cardiovascular/Cardiopulmonary Bypass, 59(5):486-92 (2013).
Zhou et al., "Unidirectional valve patch for repair of cardiac septal defects with pulmonary hypertension," Annals of Thoracic Surgeons, 60: 1245-1249, 1995.

Jodi Perkins, "Corvia Medical and physIQ Partner in Global Phase 3 Heart Faiiure Ciinicai Trial to Leverage Navei Digital Endpoints," Press Release, 2019 Copyright, Medical Alley Association, 3 pages.
Lehner et al., "The Creation of an Interatrial Right-To-Left Shunt in Patients with Severe, Irreversible Pulmonary Hypertension: Rationale, Devices, Outcomes," Current Cardiology Reports (2019) 21: 31, https://doi.org/10.1007/s11886-019-1118-8; 9 pages.
International Search Report and Written Opinion received for International Application No. PCT/US19/69106 filed Dec. 31, 2019; Applicant: Shifamed Heidings, LLC; dated Mar. 23, 2020; 10 pages.
International Search Report and Written Opinion received for International Application No. PCT/US20/49996 filed Sep. 9, 2020; Applicant: Shifamed Holdings, LLC; dated Feb. 17, 2021; 16 pages.
International Search Report and Written Opinion received for International Application No. PCT/US20/063360 filed Dec. 9, 2020; Applicant: Shifamed Holdings, LLC; dated Apr. 5, 2021; 13 pages.
International Search Report and Written Opinion received for International Application No. PCT/US20/49996 filed Dec. 11, 2020; Applicant: Shifamed Holdings, LLC; dated Apr. 8, 2021; 12 pages.
International Search Report and Written Opinion received for International Application No. PCT/US19/68354, filed Dec. 23, 2019; Applicant: Shifamed Holdings, LLC; dated Mar. 17, 2020; 11 pages.
International Search Report and Written Opinion received for International Application No. PCT/US21/16932, filed Feb. 5, 2021; Applicant: Shifamed Holdings, LLC; dated Jun. 3, 2021; 11 pages.
International Search Report and Written Opinion received for International Application No. PCT/US21/14433, filed Jan. 21, 2021; Applicant: Shifamed Holdings, LLC; dated May 14, 2021; 16 pages.
International Search Report and Written Opinion received for International Application No. PCT/US21/28926, filed Apr. 23, 2021; Applicant: Shifamed Holdings, LLC; dated Jul. 22, 2021; 16 pages.
International Search Report and Written Opinion received for International Application No. PCT/US20/12059, filed Jan. 2, 2020; Applicant: Shifamed Holdings, LLC; dated Jun. 5, 2020; 12 pages.
International Search Report and Written Opinion received for International Application No. PCT/US20/25509, filed Mar. 27, 2020; Applicant: Shifamed Holdings, LLC; dated Jun. 25, 2020; 9 pages.
International Search Report and Written Opinion received for International Application No. PCT/US20/26738, filed Apr. 3, 2020; Applicant: Shifamed Holdings, LLC; dated Jun. 30, 2020; 8 pages.
International Search Report and Written Opinion received for International Application No. PCT/US21/28931, filed Apr. 23, 2021; Applicant: Shifamed Holdings, LLC; dated Sep. 24, 2021; 20 pages.
International Search Report and Written Opinion received for International Application No. PCT/US21/27747, filed Apr. 16, 2021; Applicant: Shifamed Holdings, LLC; dated Oct. 1, 2021; 16 pages.
International Search Report and Written Opinion received for International Application No. PCT/US21/53836, filed Oct. 6, 2021; Applicant: Shifamed Holdings, LLC; dated Jan. 25, 2022; 20 pages.
Kocaturk, O. et al., "Whole shaft visibility and mechanical performance for active MR catheters using copper-nitinol braided polymer tubes," Journal of Cardiovascular Magnetic Resonance. Aug. 12, 2009, vol. 11, No. 29, p. 9, col. 1, In 5-6.
International Search Report and Written Opinion received for International Application No. PCT/US21/55191, filed Oct. 15, 2021; Applicant: Shifamed Holdings, LLC; Date of Mailing: Mar. 1, 2022; 12 pages.
Anomet Products "Conductive Nitinol Wire" Aug. 15, 2020 (Aug. 15, 2020) Retrieved from website <URL: https://helpx.adobe.com/acrobat/using/allow-or-block-links-internet.html?mv=product&mv2=acrobat>, 4 pages.
International Search Report and Written Opinion received for International Application No. PCT/US21/58996, filed Nov. 11, 2021; Applicant: Shifamed Holdings, LLC; dated Feb. 7, 2022; 23 pages.
International Search Report and Written Opinion received for International Application No. PCT/US22/19374, filed Mar. 8, 2022; Applicant: Shifamed Holdings, LLC; dated Jun. 24, 2022; 11 pages.

(56) References Cited

OTHER PUBLICATIONS

International Search Report and Written Opinion received for International Application No. PCT/US22/35764, filed Jun. 30, 2022; Applicant: Shifamed Holdings, LLC; dated Sep. 19, 2022; 10 pages.

* cited by examiner

ADJUSTABLE INTERATRIAL SHUNTS AND ASSOCIATED SYSTEMS AND METHODS

CROSS-REFERENCE TO RELATED APPLICATION(S)

This application is a 35 U.S.C. § 371 U.S. National Phase application of International Patent Application No. PCT/US2021/047573, filed Aug. 25, 2021, titled ADJUSTABLE INTERATRIAL SHUNTS AND ASSOCIATED SYSTEMS AND METHODS, which claims the benefit of U.S. Provisional Patent Application No. 63/070,007, filed Aug. 25, 2020, each of which is herein incorporated by reference in its entirety.

TECHNICAL FIELD

The present technology generally relates to implantable medical devices and, in particular, to implantable interatrial systems and associated methods for selectively controlling blood flow between the right atrium and the left atrium of a heart.

BACKGROUND

Implantable devices used in the medical field can be intended to remain temporarily implanted for minutes, hours, or days, or permanently implanted for several years. Examples of such devices include stents, shunts, and pacing leads. These medical devices often require several characteristics that can include corrosion resistance, biocompatibility, and electrical conductivity. Additionally, these medical devices generally require a capability of being catheterized such that they can be maneuvered through tortuous paths, such as those of veins or arteries, to reach and be deployed into their target anatomy. At times, a medical device may (additionally) possess a shape memory effect, such that it transitions toward a predetermined geometry upon reaching a predetermined temperature, sometimes coinciding with body temperature. The shape memory effect is achieved when the entire implant, or portions thereof, are deformed to store thermo-elastic energy that is subsequently released, the deformation being recovered upon the application of heat.

Superelastic and shape memory materials have been used extensively in medical devices for a variety of applications. At times, these applications involve delivery of an electric potential or heat to selected regions of the body to achieve a desired effect. In some applications, it is desirable to direct the electric potential or heat to one or more selected portions of the medical device, corresponding to the selected regions of the body. A challenge with superelastic and shape memory materials is that they are typically poorly electrically and thermally conductive, and may require a substantial amount of applied energy to achieve the desired effect. At times, the amount of energy delivered to achieve the desired effect may increase the risk of injury to the body, such as by electric shock or thermal insult.

One approach to reduce the amount of required energy for the implantable medical device is to improve the conductivity of the superelastic or shape memory material. Conductivity may be improved by using a combination of a conductive material with the superelastic or shape memory material. One example of combined materials to promote electrical conduction is drawn filled tube (DFT) or drawn brazed strand (DBS) used in pacemaker leads. A DFT includes an outer shell of a first material that is filled with a second material having a higher electrical conductivity than the first material. In such conventional DFTs, the energy required to achieve the desired heating effect of the outer shell material is reduced, but the energy is conducted relatively uniformly throughout the body of the DFT. Thus, the use of a conventional DFT may still require too much energy for the medical to achieve the target electric potential or temperature at the selected portion(s) of the superelastic or shape memory material.

Another use of a shape memory material is as an actuator. Such actuators are often actuated electrically, with application of electric current resulting in resistive (Joule) heating to generate the shape memory effect. Deactivation of the actuator typically occurs by free convective heat transfer to the ambient environment. Shape memory material actuation is often asymmetric in the time domain, with a relatively fast actuation time and a slow deactivation time. One method that seeks to improve (reduce) deactivation time is "lagging," wherein a thermal paste is applied to the shape memory material to rapidly transfer heat away by conduction. While this method may result in a reduction in deactivation time and a more symmetric activation profile in the time domain, one problem with this method is that the current required to achieve a given actuation force is increased.

It would be beneficial to overcome these challenges, to reduce the total amount of required energy for the medical device, and to improve delivery of energy to the preferred portions thereof.

SUMMARY

The present disclosure includes a body including a shape memory material for use in accomplishing the objects set out hereinabove. The body includes a layer of relatively conductive material forming a biased electrical and/or thermal conductive path that has one or more gaps that define a discontinuity in the layer, such that the resistivity of the conductive path is greater at the discontinuity. The position(s) of the gaps can be correlated to portions of the body that are configured to store thermo-elastically-recoverable material that promote a shape change when heated. The body may be configured for resistive and/or thermal heating to undergo the shape change. The variation in resistivity along the conductive path provides several advantages. An advantage of the present disclosure is that the body may be preferentially heated at one or more regions that undertake a relatively greater storage of thermo-elastic energy when the body changes shape. Another advantage of the present disclosure is that a total amount of energy required to generate the shape change in the body may be reduced. Another advantage of the present disclosure is that a time required to generate the shape change in the shape memory material may be reduced (for a given applied energy).

In one aspect of the present disclosure, a medical device includes an elongate member (e.g., wire/strut) that includes a base material formed of shape memory material having a first electrical resistivity; an outer layer positioned about the base material and extending along a length of the elongate member, the outer layer including a conductive material having a second electrical resistivity smaller than the first electrical resistivity; and a gap in the outer layer defining one or more discontinuities in the outer layer. In some embodiments, a portion of the shape memory material is configured to undergo a shape memory change. In some embodiments, the one or more discontinuities are located near a portion configured to undergo a shape memory change. In some embodiments, the base material and the outer layer together form a continuous cross-section along the length of the elongate member. In further embodiments, the cross-section at the one or more discontinues is different than the cross-section elsewhere along the elongate member, such as a length adjoining the discontinuities. In some embodiments, the one or more discontinuities are substantially void of the conductive material. In some embodiments, the one or more discontinuities, in cross section, extend fully through the outer layer. In some embodiments, in cross section, the one or more discontinuities comprise an amount of conductive material not greater than about 10% of the amount present in the other portions of the outer layer. In some embodiments, the one or more discontinuities comprise a third material that has a third electrical resistivity that is greater than the second electrical resistivity. In some embodiments, the base material comprises a central portion of the elongate member, and the outer layer comprises an annular layer thereon. In further embodiments, in cross section, the annular layer is substantially continuous about the central portion. In some embodiments, the first electrical resistivity is at least about 10 times greater than the second electrical resistivity. In some embodiments, the shape memory material is Nitinol residing primarily in the martensite- or R-phase below about 40 Celsius (° C.). In some embodiments, the shape memory material has a transformation start (e.g., austenite start) temperature above about 42° C. In some embodiments, the conductive material comprises Ag, Au, W, Pt, Pd, Ni, Ta, Ti, Cu, Fe, Co, Cr, Mo, Rh, Nb, or blends of these materials. In some embodiments, the conductive material and/or the shape memory material are biocompatible. In some embodiments, the gap is an air gap or void space. In some embodiments, the gap is formed of the shape memory material.

In one aspect of the present disclosure, a system for implantation in a patient includes a body that includes one or more struts formed of a shape memory material, the body having a portion that is configured to undergo a shape memory change; and an outer layer positioned about the body, the outer layer including a conductive material defining a conductive path along a length of the body and at least one interruption in the conductive path having a relatively higher resistivity than that of the conductive material. In some embodiments, the interruption is void of the conductive material. In some embodiments, the interruption comprises the shape memory material. In some embodiments, the interruption is positioned near the portion configured to undergo the shape memory change. In some embodiments, the system further includes an energy source coupled with the body and/or the conductive path, the energy source configured to delivery energy to heat the shape memory material. In further embodiments, the energy source is configured to delivery electrical energy to resistively heat the shape memory material. In further embodiments, the energy source is configured to delivery thermal energy to heat the shape memory material. In some embodiments, the conductive material is electrically conductive. In some embodiments, the conductive material is thermally conductive. In some embodiments, the energy source is configured to be remotely coupled with the body and/or the conductive pathway. In some embodiments, the energy source is electrically coupled with the body and/or the conductive pathway. In some embodiments, the body comprises a phase change section configured to change shape in response to application of heat. In some embodiments, a portion of the phase change section is in the shape of a meander, undulation, and a combination of the same. In some embodiments, at least one interruption is positioned in a region of the phase change section. In some embodiments, the energy source is configured to discharge electrical energy to the body. In some embodiments, the energy source is a supercapacitor.

In one aspect of the present disclosure, a method of preferentially heating a portion of a shape memory medical device includes delivering energy through a conductive pathway of an elongate member of the medical device, the conductive pathway formed of a conductive material and at least one interruption in the conductive material having a lower resistivity than the conductive material; and preferentially heating, with the delivered energy, a shape memory material that is coupled with the conductive pathway at the at least one interruption of the conductive pathway. In some embodiments, the conductive pathway is electrically conductive. In some embodiments, delivering energy comprises applying a voltage. In some embodiments, the conductive pathway is thermally conductive. In some embodiments, delivering energy comprises directing an energetic beam to impinge upon the conductive pathway. In some embodiments, the method further includes, by the preferential heating, generating a shape memory change in at least a portion of the shape memory material. In some embodiments, generating the shape memory change is at the at least one interruption.

In one aspect of the present disclosure, a method of making a composite element for use in an implantable medical device includes forming at least one bend in an elongate body that comprises a shape memory material, to define a first geometry; thermo-mechanically treating the elongate body to define a shape set of the shape memory material in the first geometry; coating the elongate body with a conductive material that has a resistivity that is relatively less than that of the shape memory material; and at least partially removing the conductive material from a portion of the elongate body to form a conductive pathway having at least one interruption therein. In some embodiments, the at least one interruption is formed near the at least one bend in the elongate body. In some embodiments, the at least one interruption is formed to have a resistivity that is relatively higher than the conductive material. In some embodiments, the coating comprises material joined to the body by cladding, brazing, welding, painting, sputtering, physical vapor deposition, or chemical vapor deposition. In some embodiments, forming the at least one bend and/or the heat treating sequentially follows the coating and the at least partially removing the conductive material.

DETAILED DESCRIPTION

Figure 1:
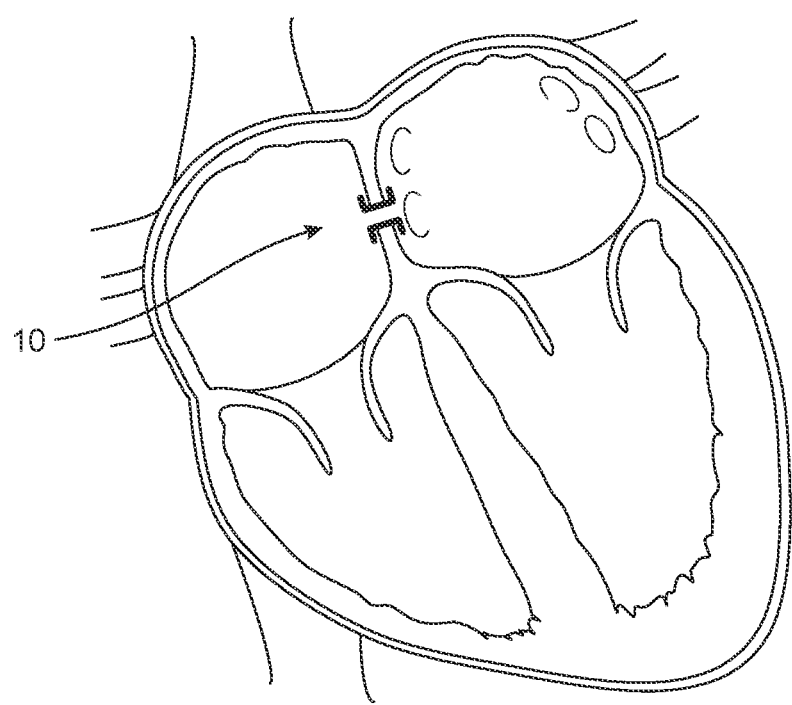
FIG. 1 is a schematic illustration of an interatrial device implanted in the heart and configured in accordance with an embodiment of the present disclosure.

The present technology is generally directed to an implantable medical device that includes a composite body formed at least partially of a shape memory material, where the composite body has a variable conductivity (and thus a variable resistance) path for preferential heating of selected portions thereof. In some embodiments, the composite body is formed of a material having a conductivity that is higher than (and thus a resistivity that is lower than) that of the shape memory material. In some embodiments, the implantable medical device is configured to undergo a shape change while implanted in a body, and the preferential heating occurs at regions of decreased conductivity and increased resistance in the conductive path. The preferential heating may be directed to portions of the composite body that undergo (substantial) strain during/following the shape change. In some embodiments, the variability in the conductive path (e.g. increased resistance) is formed by a selected change (e.g., reduction) in the presence of second material, with respect to remaining portions of the conductive path.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "about" and "approximately" are used herein to mean the stated value plus or minus 10%.

As used herein, the terms "interatrial device," "interatrial shunt device," "IAD," "IASD," "interatrial shunt," and "shunt" are used interchangeably to refer to a device that, in at least one configuration, includes a shunting element that provides a blood flow between a first region (e.g., a LA of a heart) and a second region (e.g., a RA or coronary sinus of the heart) of a patient. Although described in terms of a shunt between the atria, namely the LA and the RA, one will appreciate that the technology may be applied equally to devices positioned between other chambers and passages of the heart, between other parts of the cardiovascular system, or between other parts of the body. For example, any of the shunts described herein, including those referred to as "interatrial," may be nevertheless used and/or modified to shunt between the LA and the coronary sinus, or between the right pulmonary vein and the superior vena cava. Moreover, while applications of the disclosure herein primarily describe medical devices for shunting blood in the heart, the present technology can be readily adapted for medical devices to shunt other fluids—for example, devices used for aqueous shunting, or cerebrospinal fluid shunting. The present technology may also be adapted to a variety of implanted medical devices in addition to shunts. For example, the present technology may improve the functionality of self-guided and/or steerable devices (e.g., catheters), by reducing the cross-sectional size of electrical components and/or reducing power requirements of the device.

As used herein, the terms "flow control element" and "flow restrictor" are used interchangeably to refer to any structure that can change the flow resistance through a shunt lumen or flow path.

As used herein, the term "geometry" can include the size and/or the shape of an element and/or body. Accordingly, when the present disclosure describes a change in geometry, it can refer to a change in the size of an element (e.g., moving from a smaller circle to a larger circle), a change in the shape of an element (e.g.; moving from a circle to an oval), and/or a change in the shape and size of an element (e.g., moving from a smaller circle to a larger oval).

The headings provided herein are for convenience only and do not interpret the scope or meaning of the claimed present technology.

A. INTERATRIAL SHUNTS FOR TREATMENT OF HEART FAILURE

Heart failure can be classified into one of at least two categories based upon the ejection fraction a patient experiences: (1) HFpEF, historically referred to as diastolic heart failure or (2) HFrEF, historically referred to as systolic heart failure. One definition of HFrEF is a left ventricular ejection fraction lower than 35%-40%. Though related, the underlying pathophysiology and the treatment regimens for each heart failure classification may vary considerably. For example, while there are established pharmaceutical therapies that can help treat the symptoms of HFrEF, and at times slow or reverse the progression of the disease, there are limited available pharmaceutical therapies for HFpEF with only questionable efficacy.

In heart failure patients, abnormal function in the left ventricle (LV) leads to pressure build-up in the LA. This leads directly to higher pressures in the pulmonary venous system, which feeds the LA. Elevated pulmonary venous pressures push fluid out of capillaries and into the lungs. This fluid build-up leads to pulmonary congestion and many of the symptoms of heart failure, including shortness of breath and signs of exertion with even mild physical activity. Risk factors for HF include renal dysfunction, hypertension, hyperlipidemia, diabetes, smoking, obesity, old age, and obstructive sleep apnea. HF patients can have increased stiffness of the LV which causes a decrease in left ventricular relaxation during diastole resulting in increased pressure and inadequate filling of the ventricle. HF patients may also have an increased risk for atrial fibrillation and pulmonary hypertension, and typically have other comorbidities that can complicate treatment options.

Interatrial shunts have recently been proposed as a way to reduce elevated left atrial pressure, and this emerging class of cardiovascular therapeutic interventions has been demonstrated to have significant clinical promise. FIG. 1 shows the conventional placement of a shunt in the septal wall between the LA and RA. Most conventional interatrial shunts (e.g., shunt 10) involve creating a hole or inserting an implant with a lumen into the atrial septal wall, thereby creating a fluid communication pathway between the LA and the RA. As such, elevated left atrial pressure may be partially relieved by unloading the LA into the RA. In early clinical trials, this approach has been shown to improve symptoms of heart failure.

One challenge with many conventional interatrial shunts is determining the most appropriate size and shape of the shunt lumen. A lumen that is too small may not adequately unload the LA and relieve symptoms; a lumen that is too large may overload the RA and right-heart more generally, creating new problems for the patient. Moreover, the relationship between pressure reduction and clinical outcomes and the degree of pressure reduction required for optimized outcomes is still not fully understood, in part because the pathophysiology for HFpEF (and to a lesser extent, HFrEF) is not completely understood. As such, clinicians are forced to take a best guess at selecting the appropriately sized shunt (based on limited clinical evidence) and generally cannot adjust the sizing over time. Worse, clinicians must select the size of the shunt based on general factors (e.g., the size of the patient's anatomical structures, the patient's hemodynamic measurements taken at one snapshot in time, etc.) and/or the design of available devices rather than the individual patient's health and anticipated response. With traditional devices, the clinician does not have the ability to adjust or titrate the therapy once the device is implanted, for example, in response to changing patient conditions such as progression of disease. By contrast, interatrial shunting systems configured in accordance with embodiments of the present technology allow a clinician to select the size—perioperatively or post-implant—based on the patient.

Accordingly, the present technology provides adjustable interatrial shunting systems. Adjustable interatrial shunting systems provided herein can include, for example, a shunting element implantable into a patient at or adjacent to a septal wall that can fluidly connect a LA and a RA of the patient to facilitate blood flow therebetween. In some embodiments, one or more aspects of the system is adjustable to selectively control blood flow through the shunting element between the LA and the RA. For example, the system can include a flow control element that can transition between a plurality of geometries (e.g., shapes, sizes, orientations, positions, etc.), with each geometry being associated with a given fluid resistance through the shunting element. In some embodiments, the flow control element can selectively change a size and/or shape of the lumen. For example, the flow control element can be configured to selectively increase a diameter of the lumen and/or selectively decrease a diameter of the lumen. Throughout the present disclosure, reference to adjusting a diameter (e.g., increasing a diameter, decreasing a diameter, etc.) can refer to adjusting a hydraulic diameter of the lumen, adjusting a diameter at a particular location of the lumen, and/or adjusting a diameter along a length (e.g., a full length) of the lumen. In other embodiments, the flow control element is configured to otherwise affect flow through the lumen. For example, in some embodiments the flow control element can at least partially block an inflow port and/or an outflow port for the lumen. Accordingly, the flow control element can be coupled to a shunting element and/or can be included within the shunting element.

B. SHAPE MEMORY ACTUATORS WITH VARIABLE RESISTANCE/CONDUCTIVE PATHS

As provided above, the adjustable shunting systems described herein can include a flow control mechanism or element for adjusting a size, shape, or other characteristic of the shunt. To do so, the flow control mechanism or element can include a shape memory actuator (also referred to as a "shape memory actuation element"). The shape memory actuator is or at least includes at least one actuation element composed of a shape memory material (e.g., a shape memory alloy, a shape memory polymer, etc.). A shape memory alloy may comprise nitinol, or an alloy derivative of nitinol (e.g., NiTiCu). Actuation of the actuation element can be generated through externally applied stress and/or the use of a shape memory effect (e.g., as driven by a change in temperature). The shape memory effect enables deformations that have altered an element from its original geometric configuration to be largely or entirely reversed during operation of the actuation element. For example, sufficient heating can produce at least a temporary change in material state (e.g., a phase change) in the actuator material, inducing a temporary elevated internal stress that promotes a shape change toward the original geometric configuration. This mechanism is referred to as thermo-elastic energy storage or thermo-elastic recovery, i.e. one in which recovery ("elasticity") of a stored energy is achieved by the application of heat to trigger a phase change that recovers the stored energy of the material. In an example, the geometric change that accompanies a change in material state may reverse deformations that have been made to the material following manufacturing. For a shape memory alloy, the change in state can be from a martensitic phase (alternatively, R-phase) at the lower temperature to an austenitic phase (alternatively, R-phase) at the higher temperature. For a shape memory polymer, the change in state can be via a glass transition temperature or a melting temperature. The change in material state can recover deformation(s) of the material—for example, deformation with respect to its original (e.g., manufactured) geometric configuration—without any externally applied stress to the actuator element. That is, a deformation that is present in the material at a first temperature (e.g., body temperature) can be partially or fully recovered and/or altered by raising the material to a second (e.g., higher) temperature. In some embodiments, upon reversion to the first temperature (and reverting material state, e.g., back to a martensitic phase), the actuator element may approximately retain its geometric configuration (e.g., it may remain in the configuration that results from the application of heat). In some embodiments, upon reversion to the first temperature the actuator element may approximately retain its geometric configuration to within 30% of the heated, thermo-elastically recovered configuration. However, when the material has returned to a relatively cooler temperature (e.g., cools to body temperature following the cessation of heat application), it may require a relatively lower force or stress to thermo-elastically deform it compared to the material at a sufficiently heated temperature, and as such any subsequently applied external stress can cause the actuator element to once again deform away from the original geometric configuration. Consequently, there are exceptions that may prevent approximately full geometric recovery. Specifically, if a force or stress is applied to the element then that force may be sufficient to prevent full geometric recovery. An example would be the installation of a second shunt (e.g. a bias shunt) in communication with the actuatable shunt. A second example would be the installation of an elastic membrane on the shunt (e.g. an impermeable blood barrier fabric).

Figure 2A:
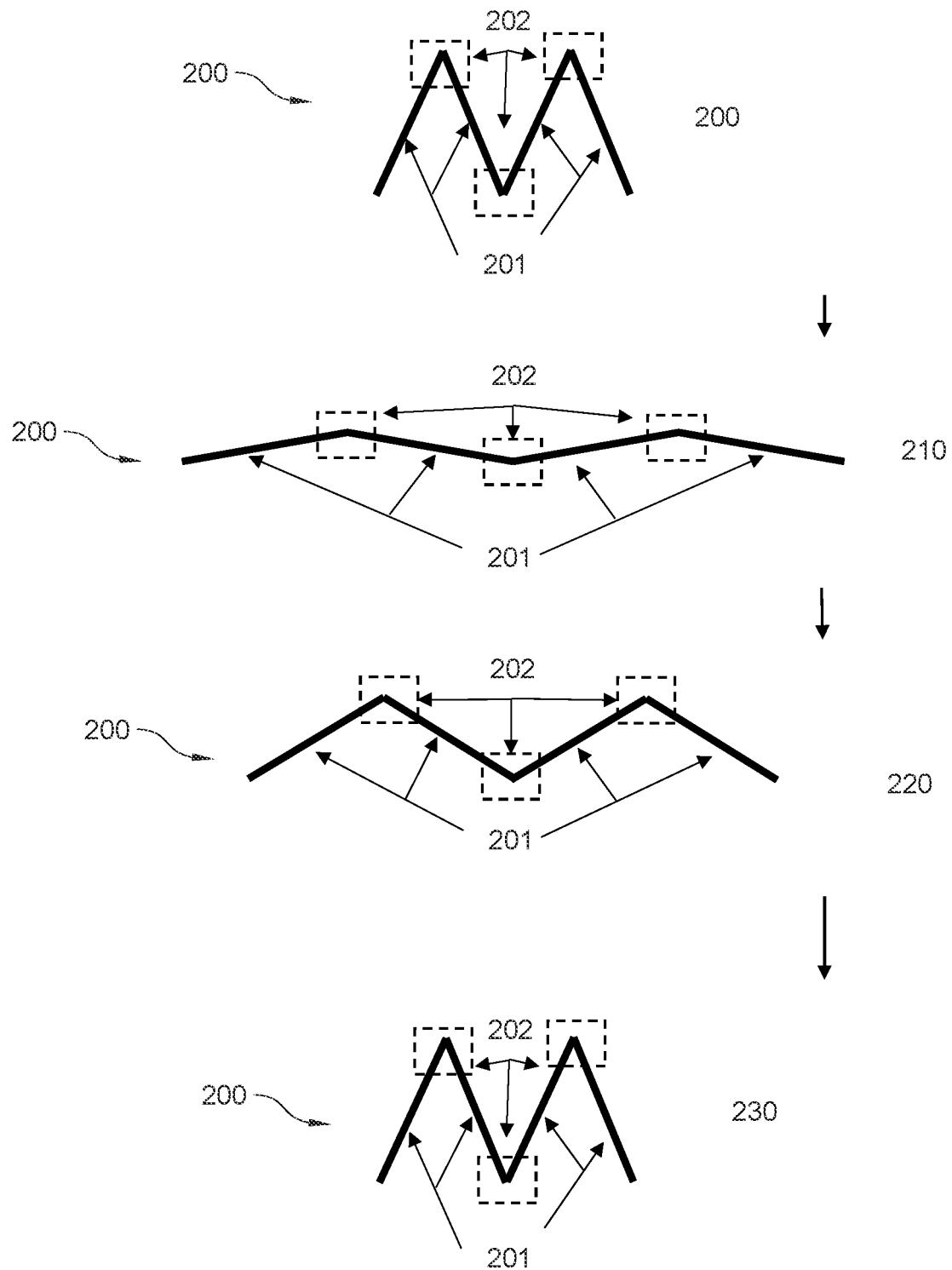
FIG. 2A is a schematic illustration of a body illustrating motion and energy storage therein, according to an embodiment of the present disclosure.

FIG. 2A shows a simplified geometric embodiment of a shape memory actuator 20 having a zig-shaped geometry for the purposes of explaining elastic and thermo-elastic energy storage. Simply put, elastic energy storage is potential energy that is stored when a force is applied to a part, such that upon release of that force the part releases the stored energy and returns to its original shape; e.g. a rubber band being stretched and then released. Thermo-elastic energy storage is that which requires heat to activate the recovery of the stored energy. In the example shown in FIG. 2A, the shape memory actuator 20 is shown in a plurality of configurations, including a first (e.g., undeformed) configuration 200, a second (e.g., stretched) configuration 210, a third (e.g., intermediate) configuration 220, and a fourth (e.g., recovered) configuration 230. The shape memory actuator 20 includes straight sections 201 and bent sections 202 (e.g., peaks). The straight sections 201 are regions where very little strain is imposed, whereas the bent sections 202 are where strain is concentrated. When a force is applied to the shape memory actuator 20 to stretch it from the first configuration 200 to the second configuration (210), some sections (e.g., the straight sections 211) remain relatively unchanged in shape, whereas other sections (e.g., the bent sections 202) preferentially deform like hinge regions. Typically, for example with Nitinol, the straight sections 201 would define regions with less than approximately 1% material strain, whereas the bent sections 202 would have material strains of approximately 1-9%. When the force is released from the shape memory actuator 20 when in the second configuration 210, the stored elastic energy is recovered but the thermo-elastic energy is retained. This results in the third configuration 230. In this configuration, the straight sections 201 are comparable in shape to their earlier shapes in the first and second configurations because they have elastically rebounded, whereas the bent sections 202 remain partially deformed with a shape somewhere between their unrestrained shape in the first configuration 200 and their deformed shape in the second configuration 210. In the third configuration, the bent sections 202 are now retaining thermo-elastic energy that can be recovered by the application of heat. Heat can be applied by any number of means; e.g. resistive heating, direct heating, induction heating, and the like. When heated, the stored energy in the peaks of the bent sections 202 is released and the bent sections close back to be approximately equal to the original shape of the first configuration 200. Consequently, the entire shape memory actuator takes on a fourth configuration 230 that approximates the first configuration 200. This process of stretching, releasing, and heating can be repeated numerous times. It is apparent to somebody skilled in the art that some small amount of thermo-elastic energy may additionally be stored in the generally straight sections, which energy will be recovered upon heating. However, advantageously to embodiments of the present disclosure, the areas that store a significantly higher amount of thermo-elastic energy (the bent sections/hinge points in this example) are the regions in which a biased conductive pathway are beneficial. For example, the biased conductive pathway forms a conductive path that is different in regions with material strain above a certain threshold (e.g. 1%) than that of regions below that threshold. Indeed, isolating (or biasing) heat towards these regions with the greatest stored thermo-elastic energy results in a large shape change while minimizing the thermal energy input to drive that change.

In order to actuate/release the stored thermo-elastic energy, heat energy must be delivered to the regions of stored thermo-elastic energy (e.g., the bent sections 202). Heat energy applied to regions without a significant amount of stored thermo-elastic energy (e.g., the straight regions 201) is therefore wasted since the application of heat in those regions does not result in a meaningful shape recovery. Consequently, to minimize the total amount of heating energy that must be applied to the system, or to reduce the time required to actuate the shape memory actuator 20, it is desirable to preferentially direct the heat energy toward the bent sections 202 and circumvent the straight sections 201.

Figure 2B:
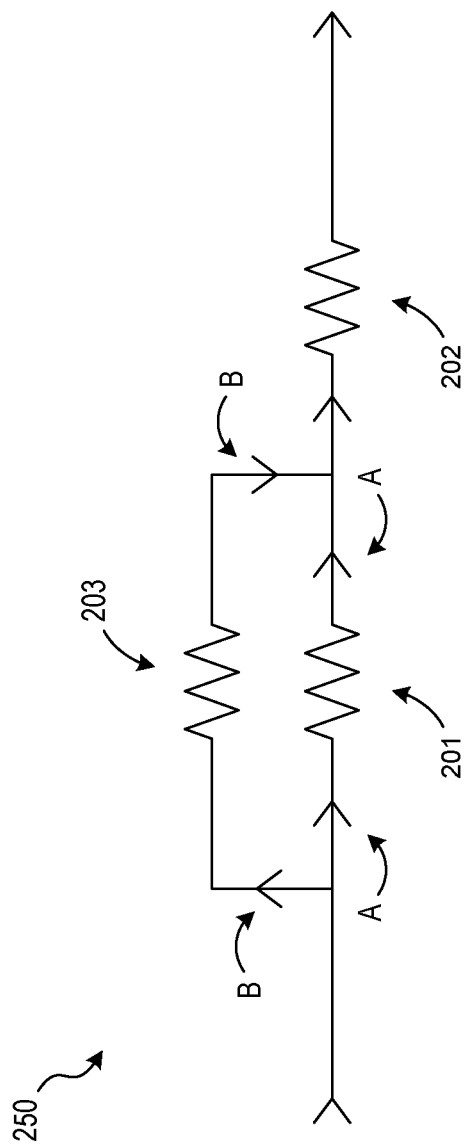
FIG. 2B is an electrical diagram schematically illustrating a variable conductivity path, according to embodiments of the present disclosure.

FIG. 2B is a schematic electrical diagram 250 illustrating the conductive pathway through the shape memory actuator 20 that results in preferentially directing heat energy toward the bent sections 202 while minimizing dissipation of heat energy in the straight sections 201. In particular, the electrical diagram 250 illustrates two paths that electrical current can flow through: a first path represented by arrows A that flows through both the straight sections 201 and the bent sections 202, and a second path represented by arrows B that flows through an electrical bypass 203 that circumvents the straight region 201. Of note, the electrical bypass 203 can be composed of a material having a higher conductivity and lower resistance than the straight sections 201. Thus, current preferentially flows through the electrical bypass 203 (i.e., flow path B) rather than the straight sections 201 (i.e., flow path A). Due to the relatively high conductivity of the electrical bypass 203, there is relatively little to no heat dissipation in the electrical bypass 203. As the current flows into the bent section 202, however, the relatively lower conductivity and higher resistance of the bent section 202 results in resistive heating of the bent section 202, driving actuation of the shape memory actuator 20. Moreover, because the current preferentially flows through the electrical bypass 203, the electrical bypass 203 is expected to minimize the current flowing through, and thus minimize the undesirable heat dissipation in, the straight sections 201. This is expected to further concentrate heating at the bent sections 202. Of course, some current will still flow through the straight sections 201. However, the amount of current flowing through the straight sections 201, and thus the heat lost in the straight sections 201, is reduced relative to embodiments without the electrical bypass 203. Although shown schematically, one skilled in the art will appreciate that the conductive pathway described and illustrated in FIG. 2B can be applied to shape memory actuators of various shapes using the techniques and processes described below.

The installation of a preferred conductive pathway, such as that described with respect to FIG. 2B, achieves a biased heating pathway. The preferred conductive pathway can be achieved by varying the conductive properties along the length of the shape memory actuator. For example, a conductive material can be installed along certain regions of the shape memory actuator to act as the electrical bypass described with respect to FIG. 2B. As used herein, the term "conductive material" refers to a material that has a relatively higher conductivity than the material it is covering (e.g., the shape memory material such as nitinol).

Figure 3:
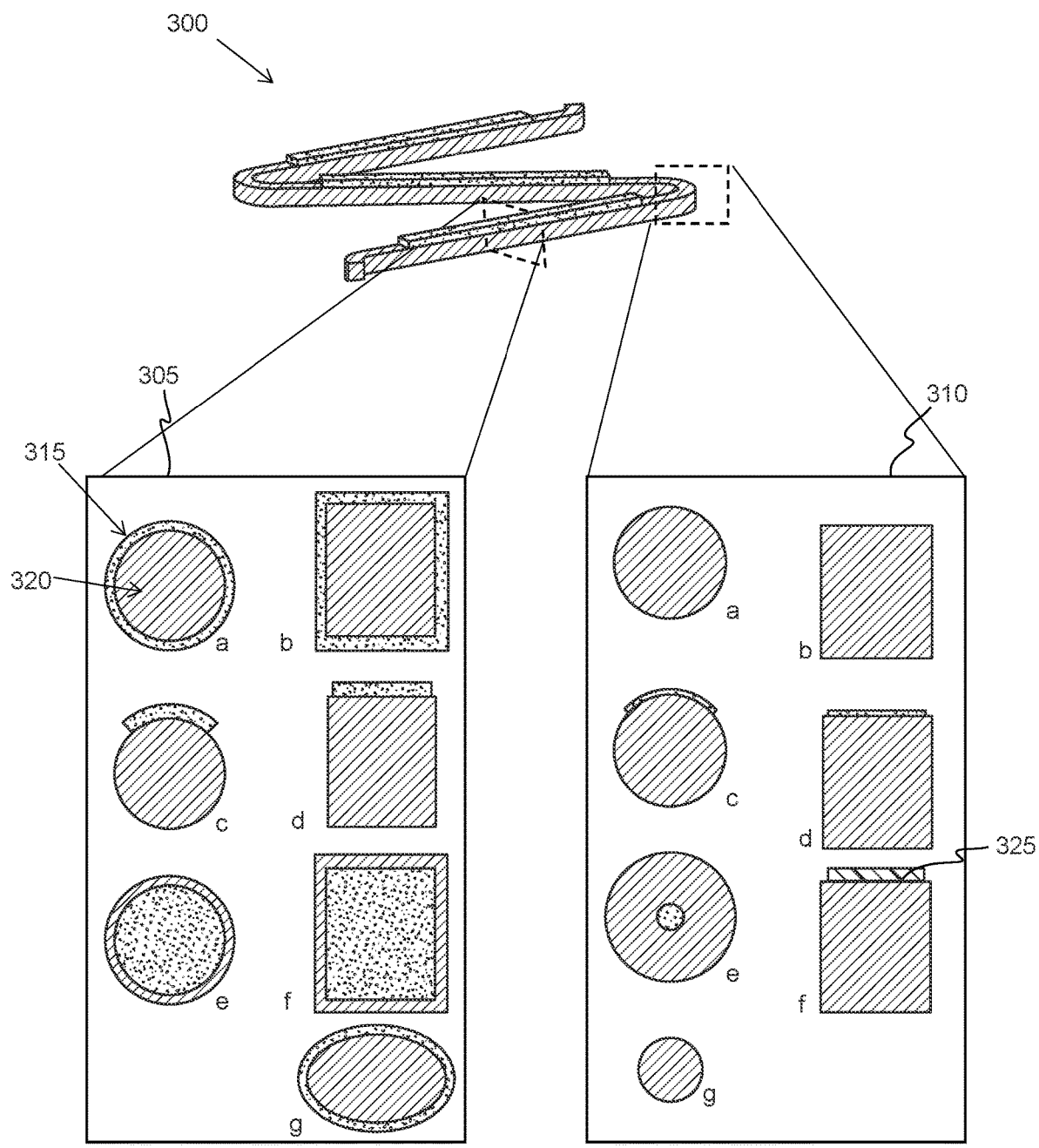
FIG. 3 is a schematic illustration of a body having a variable conductivity path, according to an embodiment of the present disclosure.

FIG. 3 illustrates a representative embodiment for varying the conductive properties along a shape memory actuator 300 using a conductive material or layer. The actuator 300 has a similar configuration to that of the shape memory actuator 20, whereby there exists regions 301 (e.g., straight regions corresponding generally to the straight sections 201 of FIG. 2A) that contain little to no stored thermo-elastic energy and regions 310 (e.g. bent regions corresponding generally to the bent sections 202 of FIG. 2A) where thermo-elastic energy is stored during the application of force. Additionally, the actuator 300 is installed with an additional layer(s) 315 of material with a different (e.g., greater) conductivity than the underlying shape memory material 320. As described below, the additional layer(s) 315 can form the electrical bypass described above with respect to FIG. 2B. As shown, the regions 305 that are generally unstrained, i.e. those which carry little to no stored thermo-elastic energy, are coated differently than the regions 310 that are highly-strained, i.e. those carrying stored thermo-elastic energy. For example, the additional conductive layer 315 is present in the unstrained region 305 whereas it is optional in the strained region 310.

The conductive material or layer 315 residing in the substantially unstrained regions 305 is of higher conductivity than the underlying shape memory material conductivity and preferably ≥5× (e.g., ≥8×, ≥10×, ≥12×, ≥15×, ≥20×, ≥50×, ≥100×, etc.) more conductive. For example, if the underlying shape memory material is Nitinol (NiTi), the additional layer (or plurality of layers) material may be silver (Ag), gold (Au), tungsten (W), platinum (Pt), palladium (Pd), nickel (Ni), tantalum (Ta), titanium (Ti), copper (Cu), iron (Fe), cobalt (Co), chromium (Cr), molybdenum (Mo), rhodium (Rh), niobium (Nb), or blends of these or other materials. Of course, the layer 315 can also include other materials and/or blends of materials not expressly mentioned herein that have a resistivity less than the underlying shape memory material (e.g., materials having a resistivity $\leq 8.20 \times 10^{-7}$ $\Omega \cdot m$) and/or a conductivity greater than the underlying shape memory material (e.g., materials having a conductivity $\geq 1.22 \times 10^6$). Table 1 below lists representative conductivities and resistances of certain materials under standard conditions.

TABLE 1

Conductivity & Resistivity of Select Materials

| Material | Conductivity (S/m) at 20° C. | Resistance (Ω · m) at 20° C. |
|---|---|---|
| NiTi | ~$1.22 \times 10^6$ | ~$8.20 \times 10^{-7}$ |
| Ag | $6.29 \times 10^7$ | $1.59 \times 10^{-8}$ |
| Au | $4.10 \times 10^7$ | $2.44 \times 10^{-8}$ |
| Pt | $9.43 \times 10^6$ | $1.06 \times 10^{-7}$ |

In some embodiments, the layer 315 is composed of a biocompatible material and/or is covered with an impermeable biocompatible coating. In some embodiments, the conductive layer 315 comprises one layer, or one material. In some embodiments, the conductive layer 315 comprises a plurality of layers, and/or a plurality of materials. In some embodiments, a given layer comprises a single material. In some embodiments, a given layer comprises at least two materials. Various embodiments of the added layers to this generally unstrained region are shown as 305a-g. There may be a conductive layering either internal or external to the shape memory material. Moreover, there may be a layer covering a singular side of the shape memory material or a plurality of sides. The cross-sectional view of this region shows a composite structure of the base shape memory material combined with a layer (or layers) of more conductive material. The conductivity of the composite cross-section is greater than the conductivity of the shape memory material alone. Consequently, electrical and heat energy flows with less resistance (obstruction) through this region, thereby resulting in a reduction in localized heating in this region relative to sections 310.

The substantially strained regions 310 may be void of the conductive material 315, or may optionally include a layer of conductive material 315. The conductivity of the optional layer in this region may be higher or lower than that of the underlying shape memory material. However, in order to promote biased heating in this region, the conductivity of the composite cross-section 310a-g must be substantially lower than the conductivity of region of generally unstrained material 305a-g. The region that includes the reduction in conductivity is at times referred to herein as an "interruption," "discontinuity," or "gap," for example in a conductive path. As shown in embodiments 310a-g, this biased conductivity composite cross section can be achieved by the complete absence (or removal) of the additional layer. Alternatively, or additionally, this reduction in conductivity in region 310 may be achieved by reducing the cross-sectional area 310a-g of the underlying shape memory material in region 310 relative to 305. Alternatively, or additionally, a material 325 having a lower conductivity than the conductive material 315 and/or the shape memory material 320 may be added to the shape memory material at region(s) 310. Alternatively, or additionally, when the same conductive layer material is chosen for areas 305 and 310, the cross-sectional area of layer material in region 310 shall be smaller than that in region 305. Alternatively, or additionally, when the layer material differs between regions 305 and 310 a thickness of the layers shall be chosen such that the conductivity of the composite cross-section 306a-g in region 310 is less than that of the composite cross-section 305a-g in region 305.

In some embodiments, the entirety of the unstrained region is installed uniformly with the conductive material (e.g., coating).

In some embodiments, the unstrained region may be installed with a non-uniform conductive material (e.g., coating). This may be a variation in a thickness of that layer, or a complete absence. The non-uniform conductive material may comprise an array of micro-dots.

In some embodiments, all regions of stored thermo-elastic energy 310 are constructed with substantially identical conductivity (within manufacturing variance). In such embodiments, all strained regions 310 are expected to be actuated substantially uniformly.

In embodiments, some regions of stored thermo-elastic energy are constructed with a conductive layer that differs from other regions of stored thermo-elastic energy. These embodiments are intended to actuate strained regions differently. Specifically, one power input will activate only a subset of the peaks, whereas a greater power input is required to activate other subset(s) of the peaks.

A conductive path can be formed externally in several ways. Conductive material can be a cladding over the shape memory material, forming a mechanical bond (e.g. DFT with shape memory core). Conductive material can be applied by optionally masking, and plating (electrochemical plating). Conductive material can be added via chemical- or physical vapor deposition (CVD or PVD). Conductive material can be added via mechanical joining methods—press fitting, welding, crimping, and the like. Conductive material can be added via evaporative methods; e.g. colloidal metal spray coating. The conductive material and shape memory material can be additively manufactured (3D printed).

Once installed, the conductive path (or pathway) can be further modified to reduce thickness in desired regions (e.g. those with large stored thermo-elastic energy). This can be achieved by mechanical means—e.g. peening, blasting, tumbling, filing, abrasive removal, and the like. This can be achieved by chemical means—acid etching, electropolishing, and the like.

A conductive path can be formed internally in several ways. In some embodiments, a shape memory material is cladded over the conductive material, forming a mechanical bond (e.g. DFT with shape memory shell). In some embodiments, a conductive material is installed in internal layer(s) via CVD or PVD. In some embodiments, a conductive material can be installed in internal layer(s) via 3D printing.

Several characteristics may be present for a conductive material. These may include a material that exhibits: a relatively high conductance compared to shape memory material (for example, 10×, 50×, 100×, or more); biocompatibility; galvanic corrosion resistance; and/or optionally, (if shape-setting or aging heat treatments will be conducted to modify the shape memory material after the conductive coating has been installed) a high melting point to withstand shape setting temperature of shape memory material (over 600° C.). In some embodiments, one or more non-conductive layers may be formed to impart one or more of the above-mentioned characteristics. The non-conductive layer(s) may comprise a ceramic, organic, or polymer material.

Figure 4:
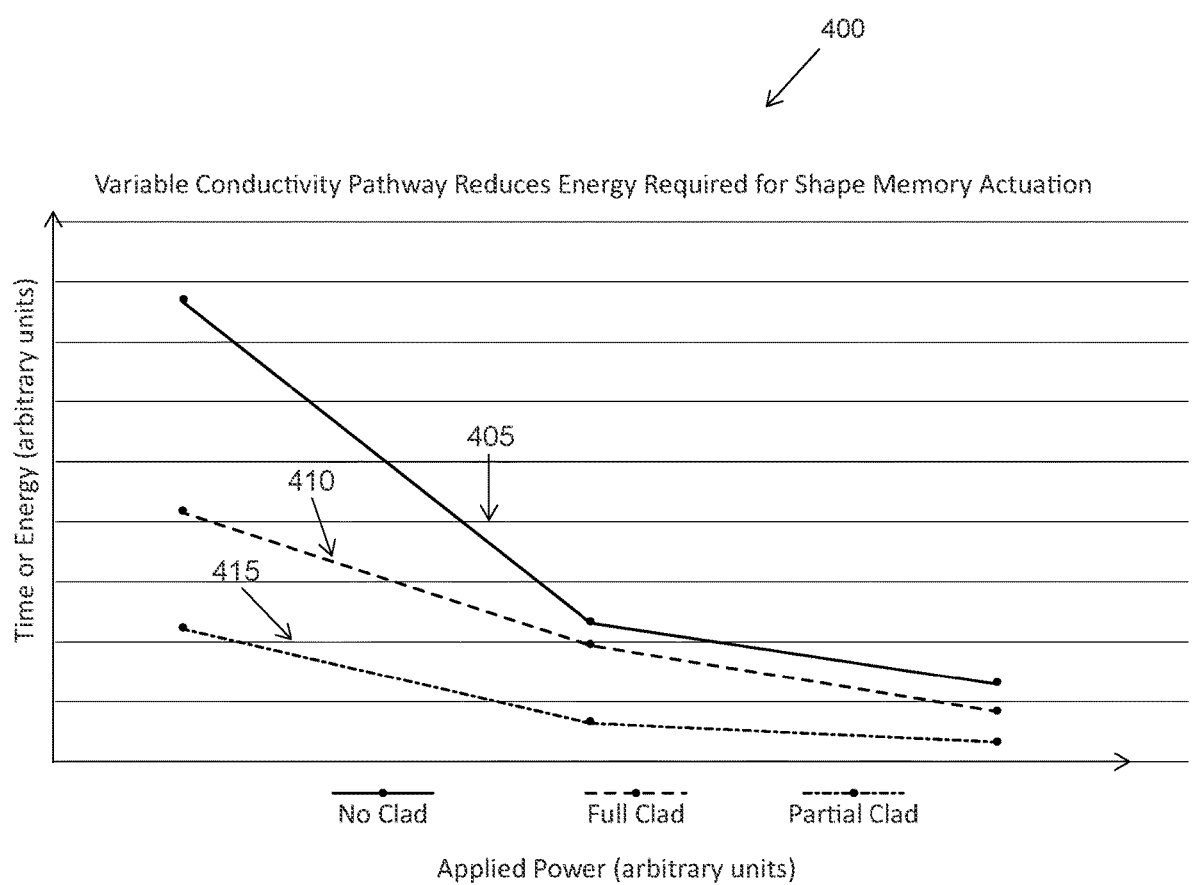
FIG. 4 is a chart depicting a relationship between time and applied energy for actuating shape memory components having a variety of variable conductive path configurations, according to an embodiment of the present disclosure.

FIG. 4 shows a representative chart 400 of the reduction in either time or energy required to actuate a shape memory component when a conductive layer is included. These data, based upon experimental results shown in FIGS. 5-7, show that a shape memory material alone (405) requires the highest energy (and time) to actuate, a shape memory implant that is completely covered with a conductive coating (410) takes relatively less energy (and time) to actuate, and a shape memory implant with conductive coating only installed in the straight sections (415) takes the least energy (and time) to actuate.

Figure 5:
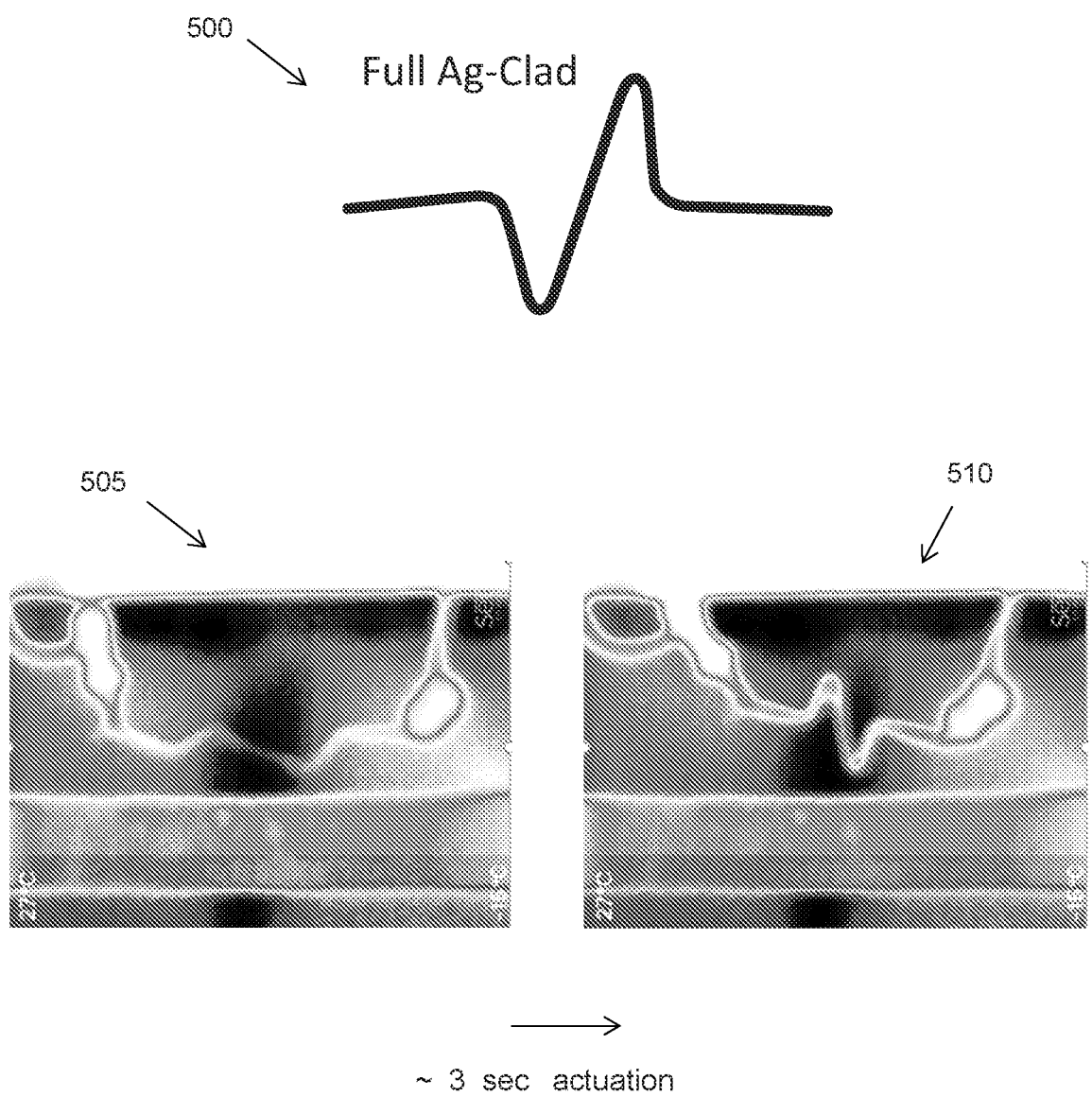
FIG. 5 depicts an actuation sequence of a shape memory component having a conductive coating, according to an embodiment of the present disclosure.
Figure 6:
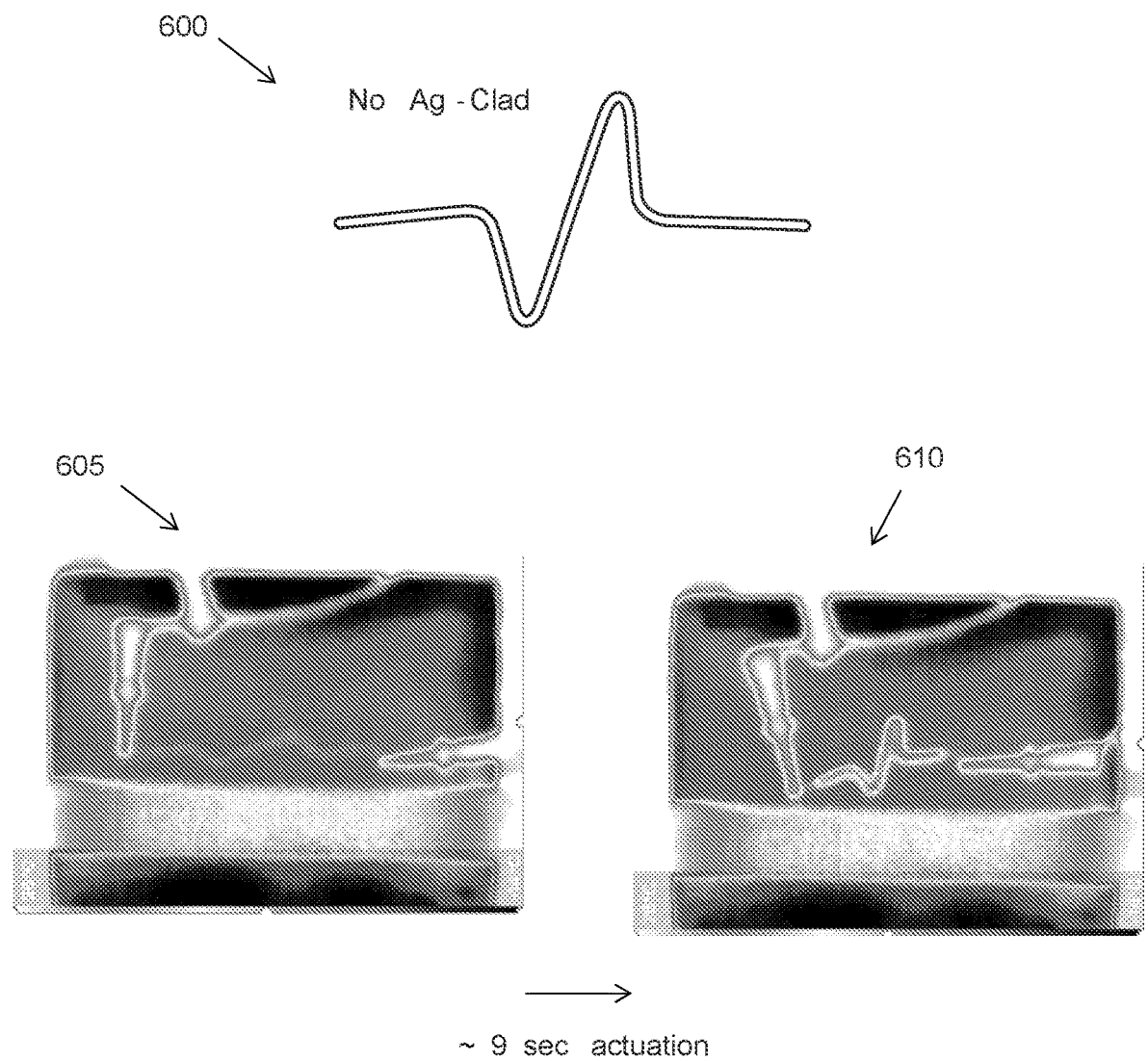
FIG. 6 depicts an actuation sequence of a shape memory component without an applied conductive coating, according to an embodiment of the present disclosure.
Figure 7:
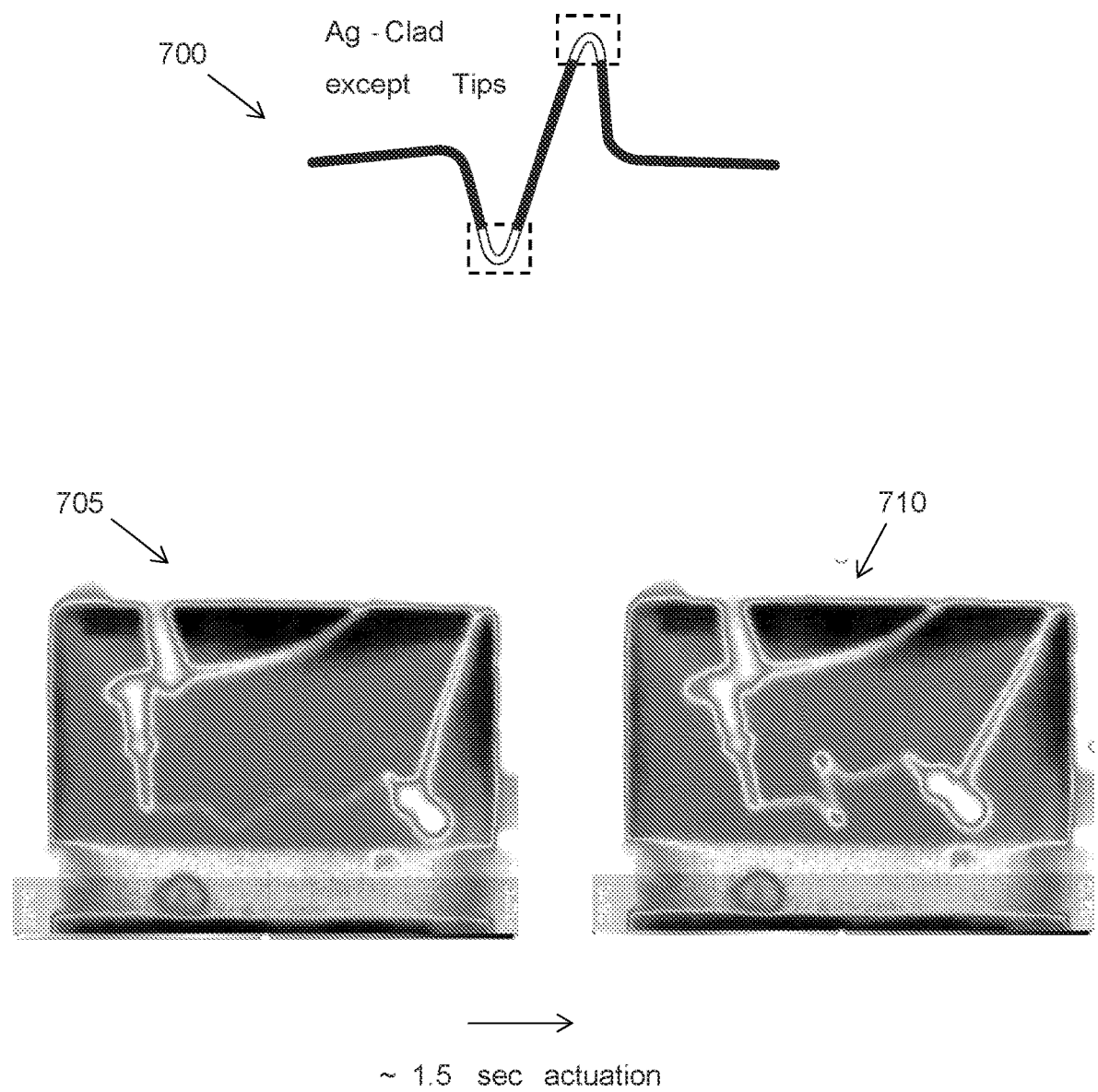
FIG. 7 depicts an actuation sequence of a shape memory component having a coating forming a variable conductivity path, according to an embodiment of the present disclosure.

FIGS. 5-7 show experimental results that illustrate advantages of a selective conductive coating (conductive coating in selective regions/portions). These experiments were conducted with experimental wires formed of a drawn-filled tube (DFT) comprised of a silver shell atop a shape memory nitinol wire. The ratio (by area) of silver-to-nitinol was approximately 5:95 in this example. The experiments included resistively (Joule) heating a wire by an energy source via coupled leads at either end, with the power applied being held constant for each experiment. The time required for actuation of the experimental wire from a deformed state to a thermally-recovered state was measured for each of three configurations that were constructed. First, one in which the silver coating was left completely intact (FIG. 5, 500). Second, one in which the silver coating was completely removed using micro-blasting (FIG. 6, 600). Lastly, one in which the silver coating was removed only at the tips of each zig using micro-blasting (FIG. 7, 700). For each configuration, a camera imaging in the infrared spectrum recorded heating within the wire, over time. For the first configuration 500 having the whole cladding, the time required to fully actuate the wire from a deformed state 505 to a recovered state 510 was approximately 3 seconds (sec). For the second configuration 600 having no cladding (all cladding removed), the time required to fully actuate the wire from a deformed state 605 to a recovered state 610 was approximately 9 sec. For the third configuration 700 having cladding selectively removed (at the tips), the time required to fully actuate the wire from a deformed state 705 to a recovered state 710 was approximately 1.5 sec. It is noted that the thermal imaging of the wire indicated that heating was occurring relatively uniformly throughout the body of the wire in configurations 500 and 600, while the heating was focused (preferentially) at the tips in the configuration 700. The images in FIGS. 5-7 demonstrate that the energy (or time) to actuate the prototype with selective coating only (FIG. 7) in the regions unstrained region (i.e. the preferred embodiment) was approximately 50% of that of the conductive coating throughout (FIG. 5), and approximately 15% of that of the shape memory material only (FIG. 6). Although this proof of concept was performed using a conveniently available ratio of Ag:NiTi, and used micro-blasting to selectively modify the conductive layer thickness, it was not the intent of these experiments to limit the design. Instead, any number of permutations of conductive material selection, ratio of conductive to SMA material, choice of location of the layer, and method of manufacturing described elsewhere herein may be used to embody this preferential heating mechanism.

C. SELECT EMBODIMENTS OF SHUNTING SYSTEMS WITH SHAPE MEMORY ACTUATORS

As provided above, the present technology includes shape memory actuators (e.g., shape memory actuation elements) having a region of highly conductive material to improve performance, such as by reducing the energy needed to actuate the shape memory actuators. The shape memory actuation element can be processed such that a transition temperature at which a change in state occurs (e.g., the austenite start temperature, the austenite final temperature, etc.) is above a threshold temperature (e.g., body temperature). For example, the transition temperature can be set to be about 42 deg. C., about 45 deg. C., about 50 deg. C., about 55 deg. C., about 60 deg. C., or another higher or lower temperature. In some embodiments, the actuator material is heated from body temperature to a temperature above the austenite start temperature (or alternatively above the R-phase start temperature) such that an upper plateau stress (e.g., "UPS_body temperature") of the material in a first state (e.g., thermoelastic martensitic phase, or thermoelastic R-phase at body temperature) is lower than an upper plateau stress (e.g., "UPS_actuated temperature") of the material in a heated state (e.g., superelastic state), which achieves partial or full geometric recovery. For example, the actuator material can be heated such that UPS_actuated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase at body temperature) is lower than a lower plateau stress (e.g., "LPS") of the material in a heated state (e.g., superelastic state), which achieves partial or full geometric recovery. For example, the actuator material can be aged such that LPS_activated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase) is higher than a lower plateau stress of the material in a heated state, which achieves partial geometric recovery. For example, the actuator material can be aged such that LPS_activated temperature<UPS_body temperature.

Figure 8:
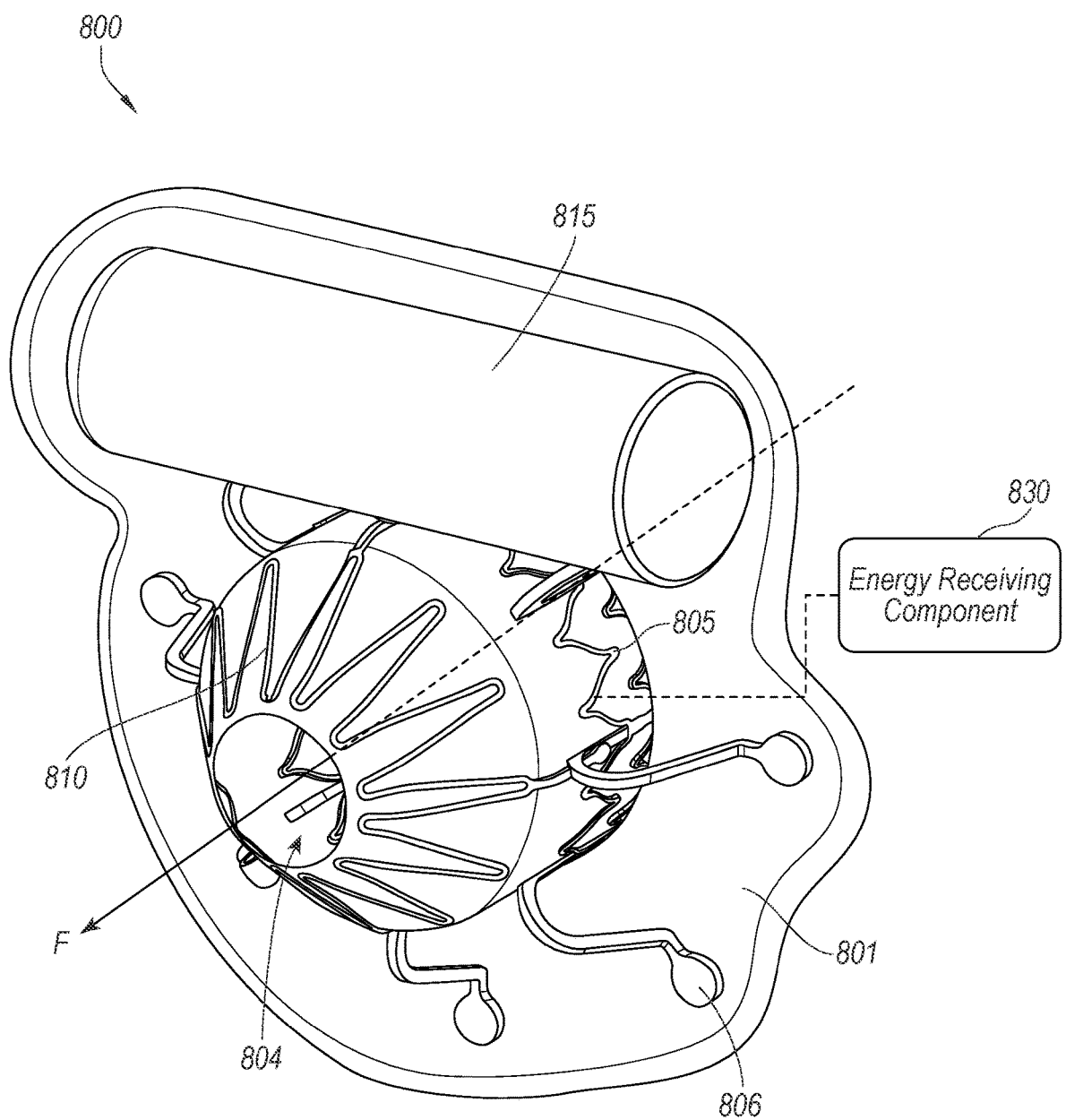
FIG. 8 is a schematic illustration of an interatrial shunting device configured according to an embodiment of the present disclosure.

FIG. 8 is a schematic illustration of an interatrial shunting system 800 ("system 800") configured in accordance with embodiments of the present technology. The system 800 includes a shunting element 805 defining a lumen 804 therethrough. When implanted in a septal wall 801, the system 800 fluidly connects the left atrium LA and the right atrium RA via the lumen 804. When the system 800 is implanted to treat HFpEF, blood generally flows through the lumen 804 in a flow direction F (e.g., from the left atrium LA to the right atrium RA). The system 800 includes a flow control mechanism 810 that is coupled to the shunting element 805 and is configured to change in geometry and/or size in order to adjust flow through the lumen 804. The flow control mechanism 810 may be adapted to adjust an orifice (end), and/or the lumen, of the shunting element 805. The flow control mechanism 810 (which can also be referred to as a shape memory actuator or a shape memory actuation element) can include a body at least partially formed of a shape memory material, and having a variable conductivity path as described herein. The shunting element 805 can be secured in place by anchoring element(s). For example, the shunting element 805 can include one or more first anchoring elements (not shown) positioned on the left atrium side of the septal wall and one or more second anchoring elements 806 positioned on the right atrium side of the septal wall. In some embodiments, the shunting element 805 is anchored in place using anchoring elements positioned on only one side of the septal wall. In yet other embodiments, the system 800 does not include anchoring elements and the shunting element 805 is secured in place be exerting a radially outward pressure or by other suitable mechanisms.

The representative system 800 can include various electronic components. For example, the system 800 can include an energy receiving component 830 and one or more energy storage components 815. The energy receiving component 830 can be configured to receive energy from an energy source positioned internal or external to a patient's body. For example, the energy receiving component 830 can be a metallic coil adapted to receive magnetic energy (or other energy, e.g., RF or heat) transmitted to the system 800 from the internal or external source. In some embodiments, the coil can be configured to receive energy transmitted in the radiofrequency (RF) frequency range. In other embodiments, the energy receiving component 830 can be configured to receive magnetic or other forms of energy. The energy receiving component 830 can be a metallic coil of high conductivity metal such as copper or silver, or composites of these. The energy storage components 815 can be configured to store energy received by the energy receiving component 830. The energy storage components 815 can include a battery, a supercapacitor, and/or other suitable elements that can retain energy. The energy received by the energy receiving component 830 and/or stored within the energy storage components 815 can be used by the flow control mechanism 810 to adjust the flow through the shunting element 805 (e.g., by resistively heating at least a portion of the flow control mechanism 810) and/or to power other operations requiring an energy input (e.g., to power the sensors (not shown)). In some embodiments, the energy storage component(s) 815 and/or the energy receiving component 830 is coupled to the body 805 and/or the flow control mechanism 810 by a wired connection. In some embodiments, the coupling includes a connection to one or more portions of the variable conductivity path. In some embodiments, the energy storage component(s) 815 and/or the energy receiving component 830 is coupled to the body 805 and/or the flow control mechanism 810 wirelessly. Wireless coupling can comprise components adapted to use magnetic, microwave, radiofrequency (RF), or ultrasonic energy.

In some embodiments, the flow control mechanism 810 is powered and/or controlled using one or more energy sources (e.g., energy storage components) included within the system. In other embodiments, the flow control mechanism 810 is powered and/or controlled using an adjustment module or tool configured to deliver energy directly to the flow control mechanism 810. For example, in some embodiments the flow control mechanism 810 can be adjusted via one or more energy modalities. A healthcare practitioner can use the energy modality to manipulate the position of the flow control mechanism 810, thereby manipulating the flow rate between the LA and the RA. Suitable energy modalities can include, for example, magnetic, radiofrequency, ultrasonic, and the like. In some embodiments, the energy source can be positioned external to the patient such that the energy is applied non-invasively. In other embodiments, however, the energy source can be positioned within the body (e.g., via a catheter) before targeting the flow control mechanism 810 with the energy. In some embodiments, the energy is applied for a relatively short period of time (e.g., less than about 0.1 seconds, less than about 1 second, less than about 10 seconds, etc.) until the flow control mechanism 810 is in the desired position, reducing the risk that tissue and/or fluid surrounding the system 800 will overheat.

D. SELECT METHODS OF THE PRESENT TECHNOLOGY

Figure 9:
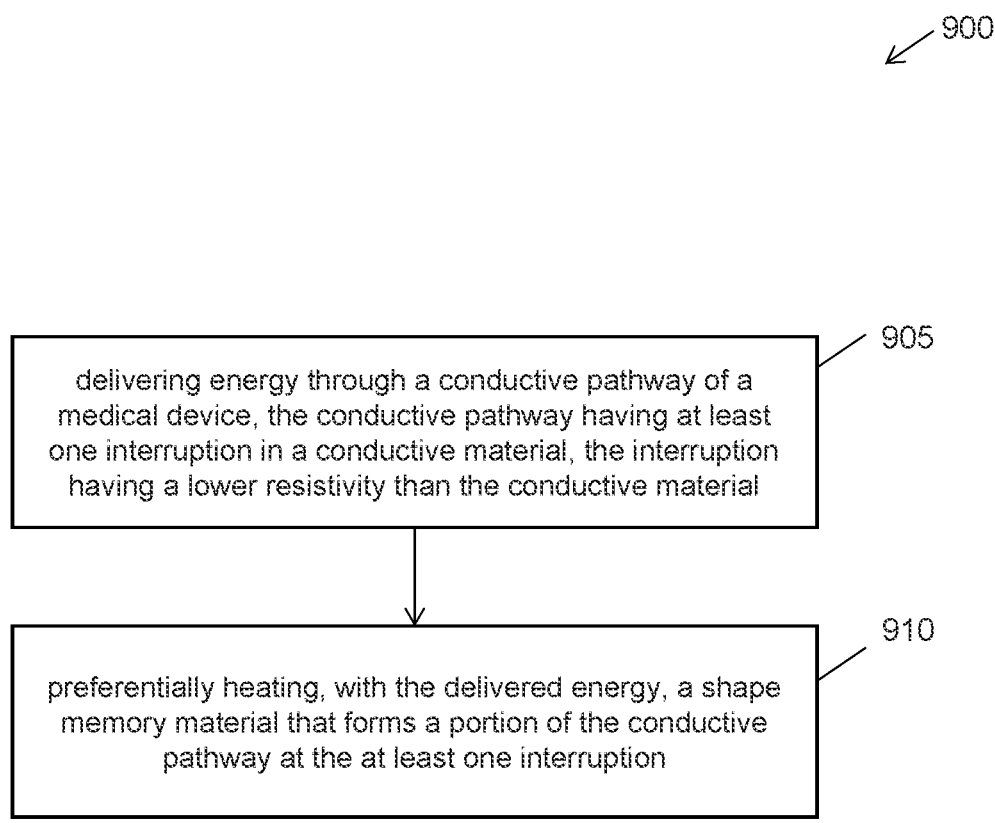
FIG. 9 is a flowchart of a method of preferentially heating a portion of a shape memory material in a medical device, according to an embodiment of the present disclosure.

FIG. 9 is a flowchart 900 of a method of preferentially heating a portion of a shape memory material in a medical device. An example operation 905 comprises delivering energy through a conductive pathway of a medical device, the conductive pathway having at least one interruption in a conductive material, the interruption having a lower resistivity than the conductive material. An example operation 910 comprises preferentially heating, with the delivered energy, a shape memory material that forms a portion of the conductive pathway at the at least one interruption.

Figure 10:
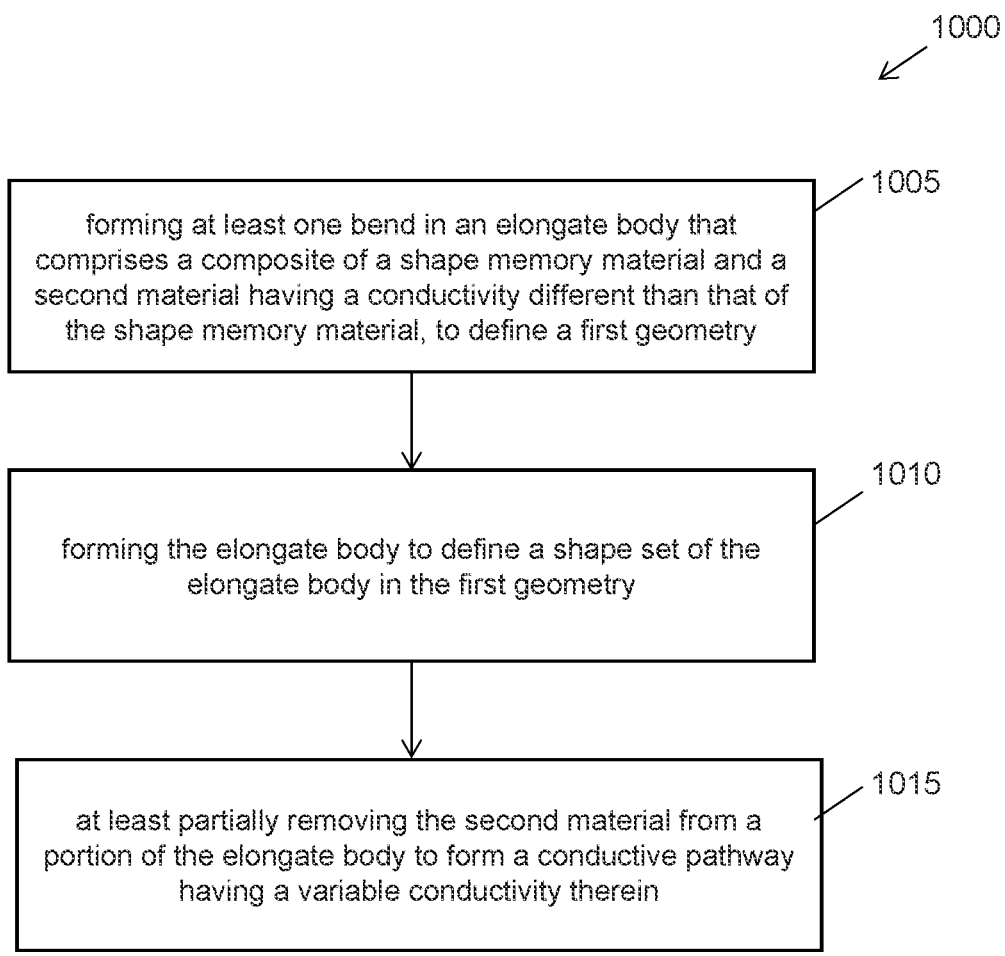
FIG. 10 is a flowchart of a method of forming a body including a shape memory material and having a variable conductivity pathway, according to an embodiment of the present disclosure.

FIG. 10 is a flowchart 1000 of a method of forming a body including a shape memory material and having a variable conductivity pathway. An example operation 1005 comprises forming at least one bend in an elongate body that comprises a composite of a shape memory material and a second material having a conductivity different than that of the shape memory material, to define a first geometry. An example operation 1010 comprises thermo-mechanically treating the elongate body to define a shape set of the elongate body in the first geometry. In some embodiments, thermo-mechanically forming comprises a heat treatment, plastic forming, or additively manufacturing (e.g., laser sintering). An example operation 1015 comprises at least partially removing the second material from a portion of the elongate body to form a conductive pathway having a variable conductivity therein. While the above are given as a sequence of operations, it will be appreciated that a fewer or greater number of operations may be performed, and/or that one or more of the operations can occur in a different sequence or excluded entirely. For example, in some embodiments the at least partially removing the second material is performed prior to the heat treating. In some embodiments, a sequence of operations includes applying the second material as a conductive coating, thermo-mechanically forming the elongate body to define a shape set, and selectively removing the conductive coating to form a variable conductivity pathway. In some embodiments, a (conductive) coating may be applied by additive manufacturing (e.g., laser sintering), PVD, electroless deposition, electrochemical deposition, spray coating, and/or cladding. In some embodiments, selective removal of the second material may comprise chemical removal, blasting, sanding, grinding, or machining. In some embodiments, a sequence of operations includes thermo-mechanically forming an elongate body to define a shape set, applying a conductive coating to the shape set body, and selectively removing the conductive coating to form a variable conductivity pathway. In some embodiments, a sequence of operations includes thermo-mechanically forming an elongate body to define a shape set, and selectively applying a conductive coating to portions of the shape set body to form a variable conductivity pathway. In another example, the hinge shape may be directly laser cut without any subsequent thermo-mechanical shaping of the elongate body.

D. EXAMPLES

Several aspects of the present technology are set forth in the following examples.

1. A medical device, including:
    an electrically-conductive member comprising—
        a base material having a first electrical conductivity; and
        a second material layer positioned in contact with the base material and extending along at least a portion of the base material, the second layer comprising an electrically-conductive material having a second electrical conductivity different than the first electrical conductivity,
        wherein the cross-sectional area of the second layer varies along the length of the member.
2. The device of example 1, wherein the second material layer is an outer material layer that interfaces with an exterior surface of the base material.
3. The device of example 1, wherein the second material layer is an inner material layer that is at least partially surrounded by the base material.
4. The device of example 1, wherein the base material and/or the second layer material is a material manufactured to have shape memory properties.
5. The medical device of example 4, wherein a portion of the shape memory material is configured to undergo a geometric change in response to a stimulus.
6. The medical device of example 5, wherein the stimulus is an applied and/or induced temperature.
7. The medical device of example 4, wherein the one or more cross-sectional variations of the second material layer are located near a portion of the member that undergoes a material strain of at least 1% during a geometric change associated with a shape memory effect.
8. The medical device of example 4, wherein the shape memory material is nitinol or an alloy derivative of nitinol (e.g. NiTiCu) manufactured to be primarily in a first material phase at temperatures below about 40° C.
9. The medical device of example 8, wherein the material phase is a martensite or R-phase.
10. The medical device of example 8, wherein the one or more cross-sectional variations of the second material layer are located near a portion of the member that undergoes a material phase change in response to a stimulus applied to the member.
11. The medical device of example 4, wherein the shape memory material is nitinol or an alloy derivative of nitinol (e.g. NiTiCu) that has been manufactured to have an austenite start temperature above about 42° C.
12. The medical device of example 1, where the second electrical conductivity is greater than the first electrical conductivity.
13. The medical device of example 1, where the second electrical conductivity is less than the first electrical conductivity.
14. The medical device of example 1, wherein at least one region of the second material layer has a cross-section of approximately zero, creating an effective gap or discontinuity in the second layer.
15. The medical device of example 14, wherein there exist multiple gaps or discontinuities of the second layer along the body of the member.
16, The medical device of example 1, wherein the electrically-conductive member is adapted to have an electrical current transmit along at least a portion of its body.
17. The medical device of example 16, wherein the member is adapted to change temperature as a result of resistive heating.
18. The medical device of example 17, wherein sections of the member having different cross-sectional areas of the second material layer experience different temperature changes in response to an electrical current applied along the member.
19. The medical device of example 18, wherein sections of the member with a smaller cross-sectional area of the second material layer experience larger temperature elevations relative to sections of the member that have a larger cross-sectional area of the second material layer.
20. The medical device of example 1, wherein the second layer forms a contiguous structure along the length of the base material.
21. The medical device of example 20, wherein the cross-sectional area of the member at one section along its length is different than the cross-sectional area at a second section along its length.
22. The medical device of example 21, wherein the differences in cross-sectional area are attributable to variations in the mass of the outer layer.
23. The medical device of example 1, wherein, in cross section, the mass of the second layer material in a first section of the member is not greater than about 10% of the mass of the second layer present in a second section of the member.
24. The medical device of example 1, wherein the electrical conductivity of a first section of the member is at least 5 times different than the electrical conductivity of a second section of the member.
25. The medical device of example 1, further comprising a third material that has a third electrical conductivity that is different (e.g., lesser) than the first and second electrical conductivity.
26. The medical device of example 1, wherein the base material comprises a central portion of the member, and the second layer comprises an annular outer layer disposed thereon.
27. The medical device of example 26, wherein for one or more sections of the member, in cross section the annular layer surrounds the base material circumferentially in a substantially homogenous manner.
28. The medical device of example 1, wherein the first electrical conductivity is at least about 8 times different than the second electrical conductivity.

29. The medical device of example 1, wherein the second layer material comprises Ag, Au, W, Pt, Pd, Ni, Ta, Ti, Cu, Fe, Co, Cr, Mo, Rh, Nb or blends of these materials.

30. The medical device of example 1, wherein the second layer material and/or the base material are biocompatible.

31. A system for implantation in a patient, including:
   a body comprising one or more bends formed of an electrically-conductive material; and
   a second material layer comprised of a second electrically-conductive material that has a different electrical and/or thermal conductivity than the body material, positioned about the body such that it is not evenly distributed across the body, resulting in a structure that has a varying electrical and/or thermal conductivity along its length.

32. The system of example 31, wherein the second material layer is an outer material layer that is disposed about the exterior surface of the body.

33, The system of example 32, wherein selected areas of the body have reduced electrical conductivity due to a reduction in cross-sectional area of the outer layer material in that area.

34. The system of example 32, wherein selected areas of the body have reduced electrical conductivity due to an absence of outer layer material in that area.

35, The system of examples 33 or 34, wherein the differences in conductivity primarily occur in regions of the body that experience material strains of at least 1% during a geometric change associated with a shape memory effect.

36. The system of example 31, wherein at least a portion of the second material layer is comprised of a shape memory material that is adapted to change its geometric configuration in response to a stimulus.

37. The system of example 31, wherein at least a portion of the body is comprised of a shape memory material that is adapted to change its geometric configuration in response to a stimulus.

38. The system of example 37, wherein a portion of the shape memory section of the body is in the shape of a meander, undulation, and/or a combination of the same.

39. The system of examples 37, wherein a reduction in second layer material cross-sectional area is located in a region of the body comprised that undergoes a material phase change following the application of energy.

40. The system of example 31, further comprising an energy source coupled with the body and/or the conductive path, the energy source configured to delivery energy the body material.

41. The system of example 40, wherein the energy source is configured to delivery electrical energy to resistively heat the body material.

42, The system of example 40, wherein the energy source is configured to delivery thermal energy to heat the body material.

43. The system of examples 40 wherein the body material is a material with shape memory properties.

44. The system of example 40, wherein the energy source is configured to be remotely coupled with the body and/or the conductive pathway.

45. The system of example 44, wherein the energy source provides thermal energy to the body via a circuit that enables induction heating.

46. The system of example 40, wherein the energy source is directly coupled with the body and/or the conductive pathway.

47. The system of examples 40, wherein the energy source is configured to discharge electrical energy to the body.

48. The system of examples 40, wherein the energy source is a supercapacitor.

49. A method of preferentially heating a portion of a shape memory medical device, the method comprising:
   delivering energy through a conductive pathway of a member of the medical device, the conductive pathway formed of a conductive shape-memory material and an adjoined second conductive material having a different conductivity than the shape memory material, with the second conductive material applied unevenly or intermittently along the body of the member; and
   preferentially heating, with the delivered energy, selected portions of a shape memory material integral to the conductive pathway.

50. The method of example 49, wherein the conductive pathway is electrically conductive.

51, The method of example 50, wherein delivering energy comprises applying a voltage and/or current.

52. The method of example 49, wherein the conductive pathway is thermally conductive.

53. The method of example 52, wherein delivering energy comprises directing an energetic beam to impinge upon the conductive pathway.

54. The method of example 49, wherein the second conductive material has a greater conductivity than the shape memory material.

55. The method of example 49, wherein the second conductive material has a lower conductivity than the shape memory material.

56. The method of example 49, wherein the uneven distribution of the second conductive material may involve gaps or discontinuities in the material.

57. The method of example 49, wherein during the energy delivery period the temperature difference between areas of the member that are preferentially heated and areas of the member that are not preferentially heated reaches at least 10° C.

58. The method of example 49, further comprising, by the preferential heating, inducing a material phase change that generates a geometric change in at least a portion of the shape memory material.

59. The method of example 58, wherein regions of the shape memory material that are not preferentially heated do not undergo a material phase change.

60. The method of example 58, wherein the generating the geometric change is driven primarily by material phase changed occurring in regions of the member where there is relatively lower cross-sectional area of the second conductive material.

61. A method of making a composite element for use in an implantable medical device, the method comprising:
   forming at least one bend in an elongate body comprised of a composite of a shape memory material and a second material surrounding the shape memory material that has a conductivity that is different than that of the shape memory material, to define a first geometry;
   directly forming or thermo-mechanically forming the elongate body to define a shape set configuration of the elongate body in a first geometry; and
   at least partially removing the second material from a portion of the elongate body to form a conductive pathway that has variable conductivity along the length of the body.

62. The method of example 61, further including the step of surrounding the shape memory material with a second material that has a conductivity that is different than that of the shape memory material.

63. The method of example 62, wherein the surrounding is achieved via cladding, brazing, welding, painting, sputtering, physical vapor deposition, or chemical vapor deposition.

64. The method of example 61, wherein the step of at least partially removing the second material from a portion of the elongate body involves completely removing the second material from one or more regions, creating gaps or discontinuities of the second material in these regions.

65. The method of example 61, wherein the removal of second material from a portion of the elongate body includes a portion near at least one bend in the elongate body.

66. The method of example 61, wherein the removal of second material from a portion of the elongate body results in that region of the elongate body having conductivity that is relatively lower than regions of the elongate body that retained the second material.

67. The method of example 61, wherein the operation of forming the at least one bend is performed after the operation of at least partially removing the conductive material.

68. A medical device, comprising:
an elongate member (e.g., wire/strut) comprising—
  a base material formed of shape memory material having a first electrical resistivity;
  an outer layer positioned about the base material and extending along a length of the elongate member, the outer layer including a conductive material having a second electrical resistivity smaller than the first electrical resistivity; and
  a gap in the outer layer defining one or more discontinuities in the outer layer.

69. The medical device of example 68, wherein a portion of the shape memory material is configured to undergo a shape memory change.

70. The medical device of example 68, wherein the one or more discontinuities are located near a portion configured to undergo a shape memory change upon the application of energy.

71. The medical device of example 68, wherein the base material and the outer layer together form a continuous cross-section along the length of the elongate member.

72. The medical device of example 71, wherein the cross-section at the one or more discontinues is different than the cross-section elsewhere along the elongate member, such as a length adjoining the discontinuities.

73. The medical device of example 68, wherein the one or more discontinuities are substantially void of the conductive material.

74. The medical device of example 68, wherein the one or more discontinuities, in cross section, extend fully through the outer layer.

75. The medical device of example 68, wherein, in cross section, the one or more discontinuities comprise a cross-sectional area of conductive material not greater than about 10% of the amount present in the other portions of the outer layer.

76. The medical device of example 68, wherein the one or more discontinuities comprise a dopant material that has a third electrical resistivity that is greater than the second electrical resistivity.

77. The medical device of example 68, wherein the base material comprises a central portion of the elongate member, and the outer layer comprises an annular layer thereon.

78. The medical device of example 77, wherein, in cross section, the annular layer is substantially continuous about the central portion.

79. The medical device of example 68, wherein the first electrical resistivity is at least about 10 times greater than the second electrical resistivity.

80. The medical device of example 68, wherein the shape memory material is martensitic or R-phase below about 40° Celsius (C).

81. The medical device of example 68, wherein the shape memory material has an austenite start temperature above about 42° C.

82. The medical device of example 68, wherein the conductive material comprises Ag, Au, W, Pt, Pd, Ni, Ta, Ti, Cu, Fe, Co, Cr, Mo, Rh, Nb, or blends of these materials.

83. The medical device of example 68, wherein the conductive material and/or the shape memory material are biocompatible.

84. The medical device of example 68, wherein the gap is an air gap.

85. The medical device of example 68, wherein the gap is formed of the shape memory material.

86. A system for implantation in a patient, the system comprising:
a body comprising one or more struts formed of a shape memory material, the body having a portion that is configured to undergo a shape memory change; and
an outer layer positioned about the body, the outer layer including a conductive material defining a conductive path along a length of the body and at least one interruption in the conductive path having a relatively higher resistivity than that of the conductive material.

87. The system of example 86, wherein the interruption is void of the conductive material.

88. The system of example 86, wherein the interruption comprises the shape memory material.

89. The system of example 86, wherein the interruption is positioned near the portion configured to undergo the shape memory change during the application of an energy.

90. The system of example 86, further comprising an energy source coupled with the body and/or the conductive path, the energy source configured to delivery energy to heat the shape memory material.

91. The system of example 90, wherein the energy source is configured to delivery electrical energy to resistively heat the shape memory material.

92. The system of example 90, wherein the energy source is configured to delivery thermal energy to heat the shape memory material.

93. The system of examples 86 or 91, wherein the conductive material is electrically conductive.

94. The system of examples 86 or 91, wherein the conductive material is thermally conductive.

95. The system of example 90, wherein the energy source is configured to be remotely coupled with the body and/or the conductive pathway.

96. The system of example 90, wherein the energy source is electrically coupled with the body and/or the conductive pathway.

97. The system of example 86, wherein the body comprises a phase change section configured to change shape in response to application of heat.

98. The system of example 86, wherein a portion of the phase change section is in the shape of a meander, undulation, and a combination of the same.

99. The system of examples 97 or 98, wherein the at least one interruption is positioned in a region of the phase change section.

100. The system of examples 90 or 96, wherein the energy source is configured to discharge electrical energy to the body.

101. The system of examples 90 or 100, wherein the energy source is a supercapacitor.

102. A method of preferentially heating a portion of a shape memory medical device, comprising:
delivering energy through a conductive pathway of an elongate member of the medical device, the conductive pathway formed of a conductive material and at least one interruption in the conductive material having a lower resistivity than the shape memory material; and
preferentially heating, with the delivered energy, a shape memory material that is coupled with the conductive pathway at the at least one interruption.

103. The method of example 102, wherein the conductive pathway is electrically conductive.

104. The method of example 103, wherein delivering energy comprises applying a voltage.

105. The method of example 102, wherein the conductive pathway is thermally conductive.

106. The method of example 105, wherein delivering energy comprises directing an energetic beam to impinge upon the conductive pathway.

107. The method of example 102, further comprising, by the preferential heating, generating a shape memory change in at least a portion of the shape memory material.

108. The method of example 107, wherein the generating the shape memory change is at the at least one interruption.

109. A method of making a composite element for use in an implantable medical device, said method comprising:
forming at least one bend in an elongate body that comprises a shape memory material, to define a first geometry;
configuring the elongate body to define a shape set of the shape memory material in the first geometry;
installing a conductive material over the elongate body, wherein the conductive material has a resistivity that is relatively less than that of the shape memory material; and
at least partially removing the conductive material from a portion of the elongate body to form a conductive pathway having at least one interruption therein.

110. The method of example 109, wherein the at least one interruption is formed near the at least one bend in the elongate body.

111. The method of example 109, wherein the at least one interruption is formed to have a resistivity that is relatively higher than the conductive material.

112. The method of example 109, wherein installing the conductive material is achieved via cladding, brazing, welding, painting, sputtering, physical vapor deposition, or chemical vapor deposition.

113. The method of example 109, wherein the operation of forming the at least one bend is performed after the operation of at least partially removing the conductive material.

114. A method of making a composite element for use in an implantable medical device, the method comprising:
forming at least one bend in an elongate body composed of a shape memory material having a first electrical conductivity; and
installing a conductive material having a second conductivity greater than the first conductivity around portions of the elongate body, wherein the portions of the elongate body are separated by one or more gaps such that the conductive material forms a non-contiguous covering of the elongate body.

115. An adjustable shunt, comprising:
a shunting element having a lumen extending therethrough configured to fluidly connect a left atrium and a right atrium of a patient; and
a flow control mechanism having an elongate actuation member configured to adjust a geometry of the lumen, the elongate actuation member comprising—
a contiguous base material formed of shape memory material having a first electrical conductivity;
an outer layer of electrically conductive material positioned about the base material and extending along a length of the base material, the outer layer having a second electrical conductivity greater than the first electrical conductivity; and
one or more at least partial gaps in the outer layer defining one or more electrical discontinuities in the outer layer.

116. The adjustable shunt of example 115 wherein a portion of the shape memory material is configured to undergo a shape memory change.

117. The adjustable shunt of example 116 wherein the one or more electrical discontinuities are located near the portion configured to undergo the shape memory change.

118. The adjustable shunt of example 115 wherein the base material and the outer layer together form a continuous cross-section between the one or more gaps.

119. The adjustable shunt of example 118 wherein a cross-section area at the one or more discontinues is less than a cross-section area having the base material and the outer layer.

120. The adjustable shunt of example 115 wherein the one or more discontinuities are substantially void of the electrically conductive material.

121. The adjustable shunt of example 115 wherein the one or more electrical discontinuities, in cross section, extend fully through the outer layer.

122. The adjustable shunt of example 115 wherein, in cross section, the one or more electrical discontinuities comprise a cross-sectional area of the electrically conductive material not greater than about 10% of the cross-sectional area in the other portions of the outer layer.

123. The adjustable shunt of example 115 wherein the one or more electrical discontinuities comprise a dopant material that has a third electrical conductivity that is less than the second electrical conductivity.

124. The adjustable shunt of example 115 wherein the base material comprises a central portion of the elongate member, and wherein the outer layer comprises an annular layer thereon.

125. The adjustable shunt of example 124 wherein, in cross section, the annular layer is substantially continuous about the central portion.

126. The adjustable shunt of example 115 wherein the second electrical conductivity is at least about 10 times greater than the first electrical conductivity.

127. The adjustable shunt of example 115 wherein the shape memory material is martensitic or R-phase below about 40° Celsius (C).

128. The adjustable shunt of example 115 wherein the shape memory material has an austenite start temperature above about 42° C.

129. The adjustable shunt of example 115 wherein the electrically conductive material comprises Ag, Au, W, Pt, Pd, Ni, Ta, Ti, Cu, Fe, Co, Cr, Mo, Rh, Nb, and/or blends thereof 130. The adjustable shunt of example 115 wherein the electrically conductive material and/or the shape memory material are biocompatible.

131. The adjustable shunt of example 115 wherein the gap is an air gap.

132. The adjustable shunt of example 115 wherein the gap is formed of the shape memory material.

133. An adjustable shunting system, comprising:
a body comprising one or more struts at last partially defining an orifice and/or lumen for enabling fluid flow therethrough, the body being formed of a shape memory material and having a portion that is configured to undergo a shape memory change;
an outer layer positioned about the one or more struts, the outer layer composed of a conductive material defining a conductive path along a length of the one or more struts; and
at least one interruption in the conductive path resulting in a relatively lower conductivity within the interruption.

134. The system of example 133 wherein the interruption is void of the conductive material.

135. The system of example 133 wherein the interruption comprises the shape memory material.

136. The system of example 133 wherein the interruption is positioned near the portion configured to undergo the shape memory change.

137. The system of example 19, further comprising an energy source coupled with the body and/or the conductive path, the energy source configured to delivery energy to heat the shape memory material.

138. The system of example 137 wherein the conductive material is electrically conductive, and wherein the energy source is configured to delivery electrical energy to resistively heat the shape memory material.

139. The system of example 137 wherein the conductive material is thermally conductive, and wherein the energy source is configured to delivery thermal energy to heat the shape memory material.

140. The system of example 137 wherein the energy source is configured to be remotely coupled with the body and/or the conductive path.

141. The system of example 137 wherein the energy source is electrically coupled with the body and/or the conductive path.

142. The system of example 133 wherein the body comprises a phase change section configured to change shape in response to application of heat.

143. The system of example 142 wherein a portion of the phase change section is in the shape of a meander, undulation, and a combination of the same.

144. The system of example 142 wherein the at least one interruption is positioned in a region of the phase change section.

145. A method of heating an actuation element of an adjustable shunt, the method comprising:
flowing electrical current through a first region of the actuation element having a first electrical conductivity, wherein the first region includes a first portion of a shape memory member; and
flowing the electrical current through a second region of the actuation element having a second electrical conductivity less than the first electrical conductivity, wherein the second region includes a second portion of the shape memory member,
wherein the electrical current preferentially heats the second portion of the shape memory member relative to the first portion of the shape memory member by virtue of the second electrical conductivity being less than the first electrical conductivity.

146. The method of example 145 wherein the first region of the shape memory actuation element includes a conductive material coupled to the first portion of the shape memory member.

147. The method of example 146 wherein the second region of the shape memory actuation element is devoid of the conductive material.

148. The method of example 146 wherein, in the first region, the electrical current preferentially flows through the conductive material relative to the first portion of the shape memory member.

149. The method of example 145 wherein the electrical current resistively heats the second portion of the shape memory member to a greater degree than the first portion of the shape memory member.

150. The method of example 145 wherein the first conductivity is at least 10 times greater than the second conductivity.

151. The method of example 145 wherein preferentially heating the second portion of the shape memory member adjusts a geometry of a lumen and/or orifice of the adjustable shunt.

152. A method of making a composite element for use in an implantable medical device, said method comprising:
forming at least one bend in an elongate body that comprises a shape memory material, to define a first geometry;
configuring the elongate body to define a shape set of the shape memory material in the first geometry;
installing a conductive material at least partially over the elongate body, wherein the conductive material has a resistivity that is relatively less than that of the shape memory material; and
at least partially removing the conductive material from a portion of the elongate body to form a conductive pathway having at least one interruption therein.

153. The method of example 152 wherein the at least one interruption is formed near the at least one bend in the elongate body.

154. The method of example 152 wherein a first conductivity of the conductive pathway at the at least one interruption is less than a second conductivity of the conductive pathway at regions with the conductive material.

155. The method of example 152 wherein the conductive material is installed via cladding, brazing, welding, painting, sputtering, physical vapor deposition, and/or chemical vapor deposition.

156. The method of example 152 wherein the wherein the operation of forming the at least one bend is performed after the operation of at least partially removing the conductive material.

CONCLUSION

Embodiments of the present disclosure may include some or all of the following components: a battery, supercapacitor, or other suitable power source; a microcontroller, FPGA, ASIC, or other programmable component or system capable of storing and executing software and/or firmware that drives operation of an implant; memory such as RAM or ROM to store data and/or software/firmware associated with an implant and/or its operation; wireless communication hardware such as an antenna system configured to transmit via Bluetooth, WiFi, or other protocols known in the art; energy harvesting means, for example a coil or antenna which is capable of receiving and/or reading an externally-provided signal which may be used to power the device, charge a battery, initiate a reading from a sensor, or for other purposes. Embodiments may also include one or more sensors, such as pressure sensors, impedance sensors, accelerometers, force/strain sensors, temperature sensors, flow sensors, optical sensors, cameras, microphones or other acoustic sensors, ultrasonic sensors, ECG or other cardiac rhythm sensors, SpO2 and other sensors adapted to measure tissue and/or blood gas levels, blood volume sensors, and other sensors known to those who are skilled in the art. Embodiments may include portions that are radiopaque and/or ultrasonically reflective to facilitate image-guided implantation or image guided procedures using techniques such as fluoroscopy, ultrasonography, or other imaging methods. Embodiments of the system may include specialized delivery catheters/systems that are adapted to deliver an implant and/or carry out a procedure. Systems may include components such as guidewires, sheaths, dilators, and multiple delivery catheters. Components may be exchanged via over-the-wire, rapid exchange, combination, or other approaches.

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. For example, although this disclosure has been written to describe devices that are generally described as being used to create a path of fluid communication between the LA and RA, the LV and the right ventricle (RV), or the LA and the coronary sinus, it should be appreciated that similar embodiments could be utilized for shunts between other chambers of heart or for shunts in other regions of the body.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An adjustable shunt, comprising:
   a shunting element having a lumen extending therethrough configured to fluidly connect a left atrium and a right atrium of a patient; and
   a flow control mechanism having an elongate actuation member configured to adjust a geometry of the lumen, the elongate actuation member comprising—
      a contiguous base material formed of shape memory material having a first electrical conductivity;
      an outer layer of electrically conductive material positioned about the base material and extending along a length of the base material, the outer layer having a second electrical conductivity greater than the first electrical conductivity; and
      one or more at least partial gaps in the outer layer defining one or more electrical discontinuities in the outer layer.

2. The adjustable shunt of claim 1 wherein a portion of the shape memory material is configured to undergo a shape memory change.

3. The adjustable shunt of claim 2 wherein the one or more electrical discontinuities are located near the portion configured to undergo the shape memory change.

4. The adjustable shunt of claim 1 wherein the base material and the outer layer together form a continuous cross-section between the one or more gaps.

5. The adjustable shunt of claim 4 wherein a cross-section area at the one or more discontinues is less than a cross-section area having the base material and the outer layer.

6. The adjustable shunt of claim 1 wherein the one or more discontinuities are substantially void of the electrically conductive material.

7. The adjustable shunt of claim 1 wherein the one or more electrical discontinuities, in cross section, extend fully through the outer layer.

8. The adjustable shunt of claim 1 wherein, in cross section, the one or more electrical discontinuities comprise a cross-sectional area of the electrically conductive material not greater than about 10% of the cross-sectional area in the other portions of the outer layer.

9. The adjustable shunt of claim 1 wherein the one or more electrical discontinuities comprise a dopant material that has a third electrical conductivity that is less than the second electrical conductivity.

10. The adjustable shunt of claim 1 wherein the base material comprises a central portion of the elongate actuation member, and wherein the outer layer comprises an annular layer thereon.

11. The adjustable shunt of claim 10 wherein, in cross section, the annular layer is substantially continuous about the central portion.

12. The adjustable shunt of claim 1 wherein the second electrical conductivity is at least about 10 times greater than the first electrical conductivity.

13. The adjustable shunt of claim 1 wherein the shape memory material is martensitic or R-phase below about 40° Celsius (C).

14. The adjustable shunt of claim 1 wherein the shape memory material has an austenite start temperature above about 42° C.

15. The adjustable shunt of claim 1 wherein the electrically conductive material comprises Ag, Au, W, Pt, Pd, Ni, Ta, Ti, Cu, Fe, Co, Cr, Mo, Rh, Nb, and/or blends thereof.

16. The adjustable shunt of claim 1 wherein the electrically conductive material and/or the shape memory material are biocompatible.

17. The adjustable shunt of claim 1 wherein the one or more gaps are air gaps.

18. The adjustable shunt of claim 1 wherein the one or more gaps are formed of the shape memory material.

* * * * *